(12) United States Patent
Pollack et al.

(10) Patent No.: US 10,101,351 B2
(45) Date of Patent: *Oct. 16, 2018

(54) METHOD FOR PROCESSING PRIORITY SAMPLES THAT PRESERVES A FIFO PROCESSING QUEUE

(71) Applicants: Benjamin Samuel Pollack, Budd Lake, NJ (US); Colin Mellars, Dover, NJ (US); Baris Yagci, Whippany, NJ (US)

(72) Inventors: Benjamin Samuel Pollack, Budd Lake, NJ (US); Colin Mellars, Dover, NJ (US); Baris Yagci, Whippany, NJ (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 624 days.

This patent is subject to a terminal disclaimer.

(21) Appl. No.: 14/390,346

(22) PCT Filed: Apr. 3, 2013

(86) PCT No.: PCT/US2013/035096
§ 371 (c)(1),
(2) Date: Oct. 2, 2014

(87) PCT Pub. No.: WO2013/152089
PCT Pub. Date: Oct. 10, 2013

(65) Prior Publication Data
US 2015/0079695 A1    Mar. 19, 2015

Related U.S. Application Data

(60) Provisional application No. 61/620,180, filed on Apr. 4, 2012.

(51) Int. Cl.
G01N 35/02    (2006.01)
G01N 35/00    (2006.01)
G01N 35/04    (2006.01)

(52) U.S. Cl.
CPC ......... G01N 35/02 (2013.01); G01N 35/0095 (2013.01); G01N 2035/0093 (2013.01);
(Continued)

(58) Field of Classification Search
CPC ............... G01N 35/02; G01N 35/0095; G01N 2035/0093; G01N 2035/0406; G01N 2035/0472; Y10T 436/113332
See application file for complete search history.

(56) References Cited

U.S. PATENT DOCUMENTS 4,699,767 A    10/1987 Aihara
2008/0271546 A1    11/2008 Miller et al.
(Continued)

FOREIGN PATENT DOCUMENTS

JP    H04-120370 U    10/1992
JP    2007 147657 A    6/2007
(Continued)

OTHER PUBLICATIONS

PCT International Search Report and Written Opinion dated Jul. 19, 2013 (8 Pages).
(Continued)

Primary Examiner — Benjamin R Whatley

(57) ABSTRACT

Methods and systems for processing samples in an analyzer utilizes a track system with a plurality of track portions. A queue of samples for processing can be handled on a first portion, while priority samples may be handled on another portion. An instrument in a module may process samples in queues and priority samples. The instrument may process priority samples while a queue of samples remains on the first portion and resumes processing the queue of samples along the first portion upon completion of processing the priority sample.

16 Claims, 13 Drawing Sheets

(52) U.S. Cl.
CPC ............... *G01N 2035/0406* (2013.01); *G01N 2035/0472* (2013.01); *Y10T 436/113332* (2015.01)

(56) References Cited

U.S. PATENT DOCUMENTS

| | | |
|---|---|---|
| 2011/0104742 A1 | 5/2011 | Fox et al. |
| 2012/0004742 A1 | 1/2012 | Wakamiya et al. |
| 2014/0370608 A1* | 12/2014 | Gelbman ............... B01L 3/545 436/47 |

FOREIGN PATENT DOCUMENTS

| | | | |
|---|---|---|---|
| JP | 2007147657 A | * | 6/2007 |
| JP | 2008 032652 A | | 2/2008 |
| JP | 2009 008552 A | | 1/2009 |
| JP | 2009008552 A | * | 1/2009 |

OTHER PUBLICATIONS

Supplementary EP Search Report dated Nov. 25, 2015 of corresponding European Application No. 13772937.2, 4 Pages.

* cited by examiner

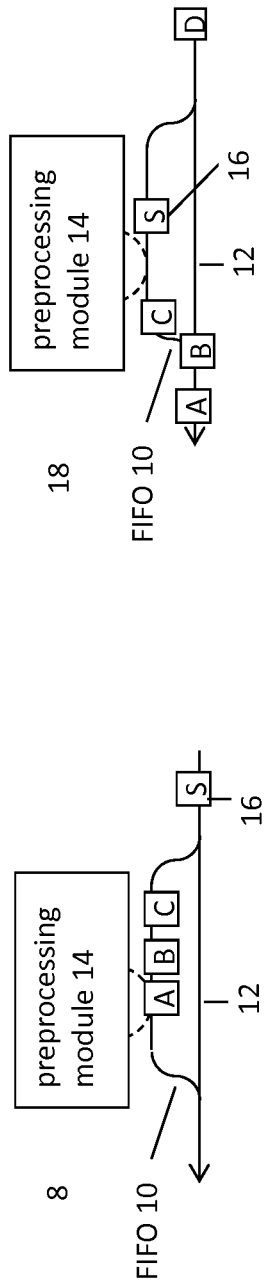
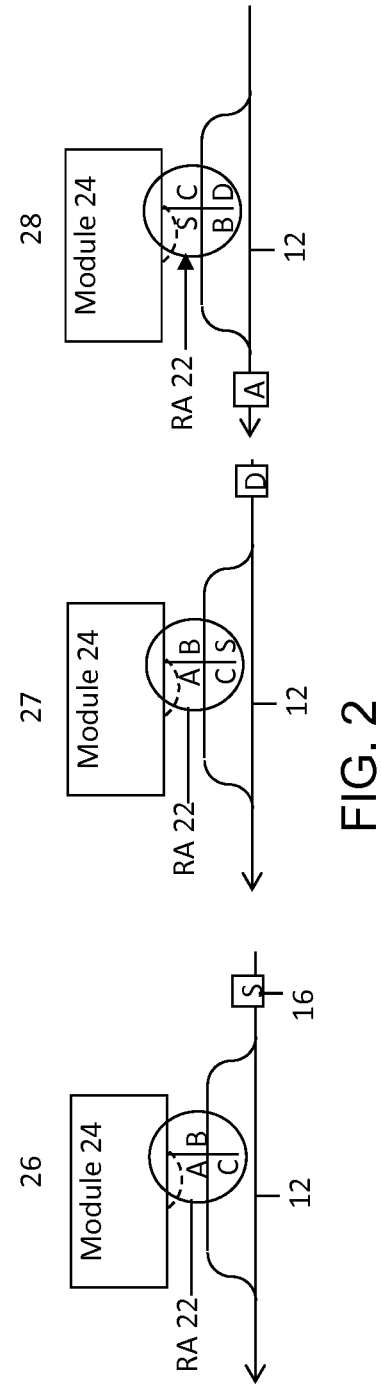
FIG. 1
FIG. 2

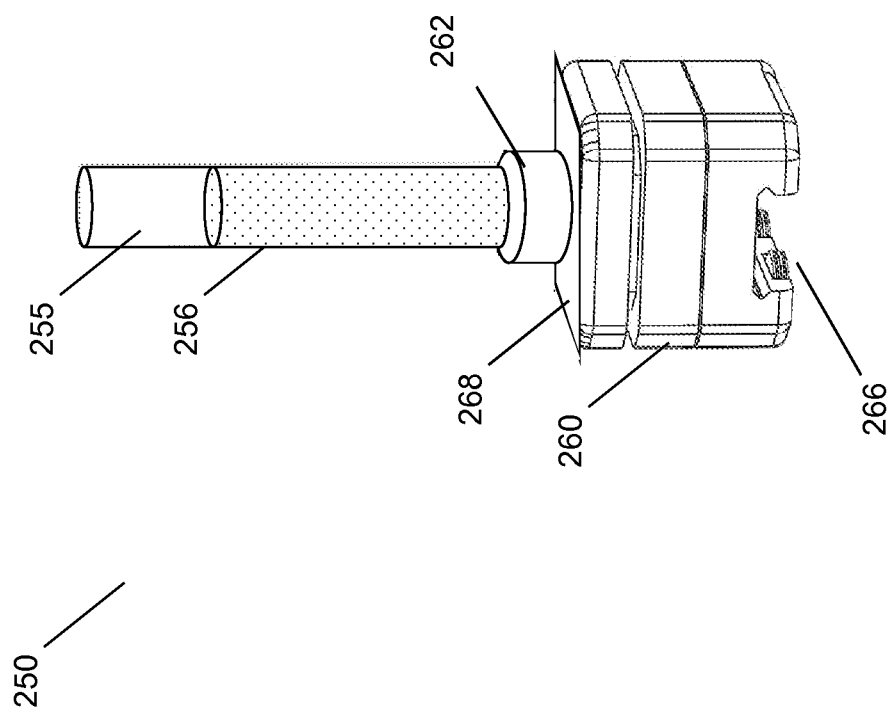

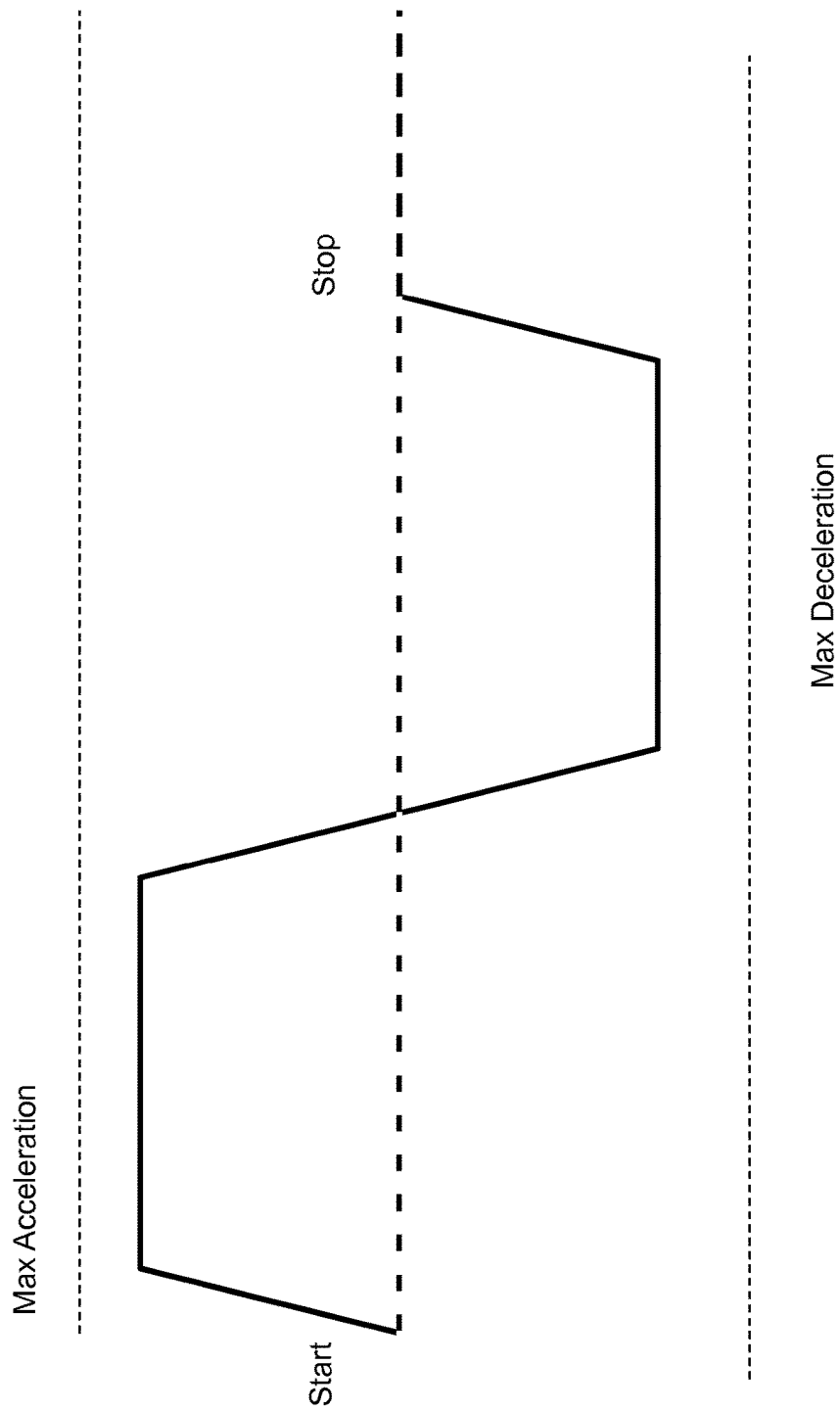

METHOD FOR PROCESSING PRIORITY SAMPLES THAT PRESERVES A FIFO PROCESSING QUEUE

CROSS-REFERENCE TO RELATED APPLICATIONS

This application claims priority to U.S. provisional application Ser. No. 61/620,180 filed Apr. 4, 2012, which is incorporated herein by reference in its entirety.

TECHNOLOGY FIELD

The present invention relates in general to an automation system for use in a laboratory environment and, more particularly to systems and methods for handling samples within the automation system that have differing priority. Embodiments of the present invention are particularly well suited, but in no way limited, to automation systems for use in an IVD environment.

BACKGROUND

In vitro diagnostics (IVD) allows labs to assist in the diagnosis of disease based on assays performed on patient fluid samples. IVD includes various types of analytical tests and assays related to patient diagnosis and therapy that can be performed by analysis of a liquid sample taken from a patient's bodily fluids, or abscesses. These assays are typically conducted with automated clinical chemistry analyzers (analyzers) onto which fluid containers, such as tubes or vials containing patient samples have been loaded. The analyzer extracts a liquid sample from the vial and combines the sample with various reagents in special reaction cuvettes or tubes (referred to generally as reaction vessels). In some conventional systems, a modular approach is used for analyzers. A lab automation system can shuttle samples between one sample processing module (module) and another module. Modules may include one or more stations, including sample handling stations and testing stations (e.g., a unit that can specialize in certain types of assays or can otherwise provide testing services to the larger analyzer, which may include immunoassay (IA) and clinical chemistry (CC) stations. Some traditional IVD automation track systems comprise systems that are designed to transport samples from one fully independent module to another standalone module. This allows different types of tests to be specialized in two different stations or allows two redundant stations to be linked to increase the volume of sample throughput available. These lab automation systems, however, are often bottlenecks in multi-station analyzers.

In an exemplary prior art system, a friction track, much like a conveyor belt, shuttles individual carrier mechanisms, sometimes called pucks, or racks of containers between different stations. Samples may be stored in sample containers, such as test tubes that are placed into a puck by an operator or robot arm for transport between stations in an analyzer along the track. This friction track, however, can only move in one direction at a time and any samples on the track will move in the same direction at the same speed. When a sample needs to exit the friction track, gating/switching can be used to move individual pucks into offshoot paths, which may be called sidecars. A drawback with this set up is that singulation must generally be used to control the direction of any given puck at each gate and switch. For example, if two pucks are near one another and only one puck should be redirected into an offshoot path, it becomes difficult to control a switch so that only one puck is moved into the offshoot path and ensure that the proper puck is pulled from the friction track. This has created the need in many prior art systems to have pucks stop at a gate so that individual pucks can be released and switched one at a time at each decision point on a track. Furthermore, additional friction tracks rely on optical identification of samples via barcodes at any decision points on the automation track. This may require a slow mechanical stop, rotate, and check process that limits the number of samples that may pass a singulated decision point.

Hard singulation slows down the overall track and increases traffic jams within the track. This leads to the need for physical queues within the track. Much like traffic on a road, traffic on the track causes an accumulation of slow-moving pucks because most of the time spent in transit during operation can be spent waiting through a line at a singulation point for switching by a gate. This leads to inefficiency in transit. Ultimately for a high volume analyzer, a substantial amount of time for each sample is spent waiting in queues at the gates on the friction track. This increases the latency experienced by each sample. Latency can be a problem for certain types of samples, such as whole blood samples, which can begin to separate or coagulate if the sample sits in the sample tube for too long.

Because pucks traditionally stop to be routed, handled, and processed, samples in prior art systems find themselves waiting in several queues before all processing on a sample is completed. These queues can grow to be quite large as the number of samples to be handled grows. Most conventional lab automation tracks maintain FIFO processing queues to buffer samples that are waiting to be processed by modules (analyzers or pre/post analytic devices). These buffers allow the track to process tubes at a constant rate even though the modules create bursts of demand.

Another problem with long queues and traffic on the friction track is the issue of handling STAT samples. A STAT sample is a sample that an operator wishes to have moved to the front of the line so that results for that sample can be returned quickly. For example, in a hospital with an emergency room, test results may be urgent for a patient awaiting treatment. In prior art friction track systems with long queues, the entire queue often must be flushed to make way for the STAT sample. This can undo several minutes worth of sorting of samples and can increase the overall latency experienced by non-STAT samples. When a STAT sample is introduced to the track, it must either wait for all of the samples in the queue to be processed, or the entire queue must be flushed back to the main track in order to allow the STAT to be processed immediately. If the queue is flushed, then the analyzer will have to abandon any work it may have already done to prepare to aspirate the queued samples, such as preparing a cuvette or aspirating a reagent. Flushing the queue is also disruptive to the automation system. A large number of samples with unprocessed work will flood onto the main track and have to be routed. Each sample must travel the complete length of the track loop in order get back to the analyzer and reenter the queue.

SUMMARY

Embodiments of the present invention may address and overcome one or more of the above shortcomings and drawbacks by providing devices and systems for transporting samples by utilizing a plurality of stopping positions accessible to an instrument in an automation system that are associated with different priorities of samples. Lower priority samples can be processed at location on a local track portion, such as an internal sidecar, that may be associated with a local queue. Meanwhile, higher priority samples can be processed at a second location that may not require the priority sample to wait through a local queue or require flushing the local queue to give the priority sample priority access to the instrument.

According to one embodiment of the invention, a method of processing samples utilizes a track system that includes an external track portion along which the samples are transported and a plurality of internal track portion. Each internal track portion intersects the external track portion to create a respective side track along which samples are transported. The steps include handling on a first internal track portion, a queue of samples for processing by a first module, handling a priority sample on a portion of the external track portion accessible to the first module for processing the priority sample. The first module is then instructed to process the priority sample. An instrument in the first module is configured to process the queue of samples along the first internal track portion and the priority sample on the portion of the external track portion accessible for processing the priority sample by the first module. The instrument in the first module processes the priority sample while the queue of samples remains on the first internal track portion and resumes processing of the queue of samples along the first internal track portion upon completion of processing the priority sample.

According to one aspect of some embodiments, the instrument can include a pipette. The instrument in the first module can be positioned on a rotating device, wherein the rotating device is configured to rotate between positions allowing for processing on the first internal track portion and the portion of the external track portion accessible by the first module. The instrument in the first module can include a linearly extending instrument configured to allow for processing on the first internal track portion and a portion of the external track portion linearly extending therefrom.

According to another aspect of some embodiments, the first module can include an in vitro diagnostics module. The queue of samples and the priority sample can include patient samples. The module can also include: (i) a sample handling module; (ii) an immunoassay module; or (iii) a clinical chemistry module.

According to another embodiment, an automation system for use in transporting samples between modules for processing includes a track system. The track system includes an external track portion along which samples are transported and a plurality of internal track portions, where each internal track portion intersecting the external track portion to create a respective side track along which samples are transported. The automation system can further include a plurality of modules, where each module includes a section of the external track portion and at least one internal track portion. When the plurality of modules is connected together, the sections of the external track portion comprise a continuous external track portion. Each of the plurality of modules can be configured to access samples on both the external track portion and one or more of the at least one internal track portions. An instrument in a first module can be configured to process a queue of samples along a first internal track portion and a priority sample on a portion of the external track portion accessible by the first module. The instrument processes the priority sample while the queue of samples remains on the first internal track portion and resumes processing of the queue of samples along the first internal track portion upon completion of processing the priority sample.

According to another embodiment, an automation system includes a plurality of automation track portions that are together configured to provide one or more paths between a plurality of analyzer stations and a plurality of carriers, each configured to traverse the plurality of track portions to transport at least one of a plurality of fluid vessels along the one or more paths to each of the plurality of stations. One or more processors are configured to, for each of the plurality of fluid vessels, determine a priority of the fluid vessel. If the fluid vessel is of a first priority, the processor directs a carrier of the plurality of carriers holding the fluid sample to stop at a first location on a first track portion. If the fluid vessel is of a second, higher priority, the processor directs the carrier to stop at a second location on a second track portion. Then, the processor requests that an analyzer station processes a fluid contained in the fluid vessel at the corresponding first or second location. Both the first and second locations are accessible to an instrument of the analyzer station.

According to one aspect of some embodiments, the first location can corresponds to the head of a queue of carriers on the first track portion. The second location can be positioned such that higher priority fluid vessels may be positioned at the second location without first flushing the queue. According to another aspect of some embodiments, the processor may only direct carriers onto the first track portion if they carry a sample vessel of the first priority.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of embodiments of the present invention are best understood from the following detailed description when read in connection with the accompanying drawings. For the purpose of illustrating embodiments of the invention, there is shown in the drawings embodiments that are presently preferred, it being understood, however, that embodiments of the invention is not limited to the specific instrumentalities disclosed. Included in the drawings are the following Figures:

FIG. 1 is a diagrammatic view illustrating multiple situations in an exemplary FIFO queue;

FIG. 2 is a diagrammatic view illustrating multiple situations in an exemplary random access queue;

FIG. 6A is a perspective view of an exemplary carrier that can be used with the embodiments disclosed herein;

FIG. 10 is an exemplary acceleration profile used by sample carriers in certain embodiments;

DETAILED DESCRIPTION OF ILLUSTRATIVE EMBODIMENTS

Figure 3:
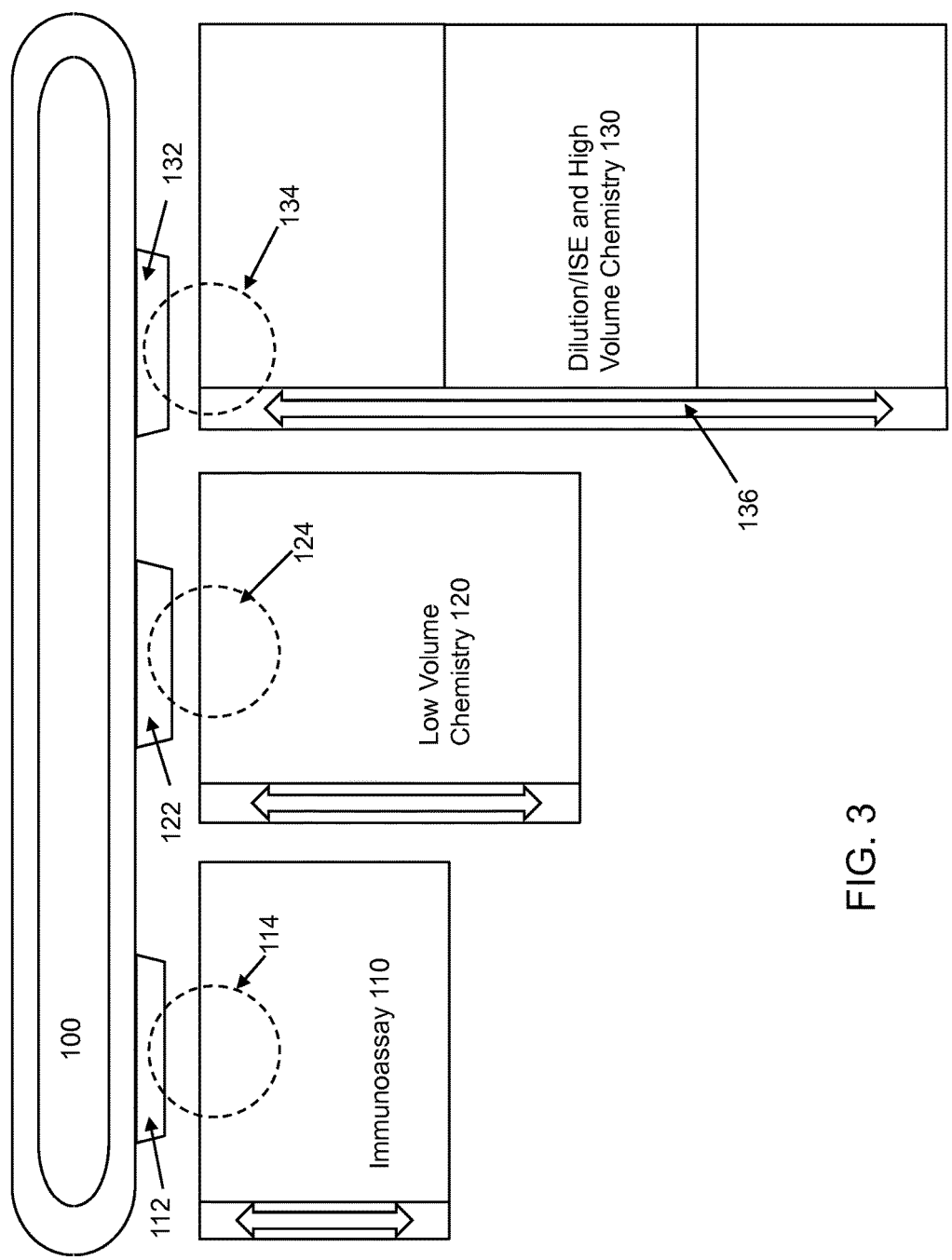
FIG. 3 is a top view of an exemplary clinical chemical analyzer geometry that can be improved by use of the automation system embodiments disclosed.

Terms and Concepts Associated with Some Embodiments

Analyzer: Automated clinical analyzers ("analyzers") include clinical chemistry analyzers, automated immunoassay analyzers, or any other type of in vitro diagnostics (IVD) testing analyzers. Generally, an analyzer performs a series of automated IVD tests on a plurality of patient samples. Patient samples may be loaded into an analyzer (manually or via an automation system), which can then perform one or more immunoassays, chemistry tests, or other observable tests on each sample. The term analyzer may refer to, but is not limited to, an analyzer that is configured as a modular analytical system. A modular analytical system includes an integrated and extendable system comprising any combinations of a plurality of modules (which can include the same type of module or different types of modules) interconnected in a linear or other geometric configuration by an automation surface, such as an automation track. In some embodiments, the automation track may be configured as an integral conveyance system on which independent carriers are used to move patient samples and other types of material between the modules. Generally, at least one module in a modular analytical system is an analyzer module. Modules may be specialized or made redundant to allow higher throughput of analytical tasks on patient samples.

Analyzer module: An analyzer module is a module within a modular analyzer that is configured to perform IVD tests, such as immunoassays, chemistry tests, or other observable tests on patient samples. Typically, an analyzer module extracts a liquid sample from a sample vessel and combines the sample with reagents in reaction cuvettes or tubes (referred to generally as reaction vessels). Tests available in an analyzer module may include, but are not limited to, a subset of electrolyte, renal or liver function, metabolic, cardiac, mineral, blood disorder, drug, immunoassay, or other tests. In some systems, analyzer modules may be specialized or made redundant to allow higher throughput. The functions of an analyzer module may also be performed by standalone analyzers that do not utilize a modular approach.

Carrier: A carrier is a transportation unit that can be used to move sample vessels (and, by extension, fluid samples) or other items in an automation system. In some embodiments, carriers may be simple, like traditional automation pucks (e.g., passive devices comprising a holder for engaging a tube or item, a friction surface to allow an external conveyor belt in the automation track to provide motive force, and a plurality of sides that allow the puck to be guided by walls or rails in the automation track to allow the track to route a puck to its destination). In some embodiments, carriers may include active components, such as processors, motion systems, guidance systems, sensors, and the like. In some embodiments, carriers can include onboard intelligence that allows carriers to be self-guided between points in an automation system. In some embodiments, carriers can include onboard components that provide motive forces while, in others, motive forces may be provided by an automation surface, such as a track. In some embodiments, carriers move along automation tracks that restrict motion to a single direction (e.g., fore and aft) between decision points. Carriers may be specialized to a given payload in an IVD environment, such as having a tube holder to engage and carry a sample tube, or may include mounting surfaces suitable to carry different items around an automation system. Carriers can be configured to include one or more slots (e.g., a carrier may hold one or a plurality of sample vessels).

Carriers/Trays/Racks: A carrier may be distinguishable from a tray, which may commonly refer to a device that does not travel along an automation track (e.g., carried by an operator) and is configured to hold a plurality of payloads (e.g., sample tubes). A rack is a general term to describe a device that is configured to hold a plurality of payloads (e.g., sample tubes). A rack may refer to a tray (when used outside an automation track) or carrier (when configured to traverse an automation track) that is configured to carry a plurality of payloads. Racks may refer to one-dimensional or two-dimensional arrays of slots, in some embodiments.

Central controller or processor: A central controller/processor (which may sometimes be referred to as a central scheduler) is a processor that is part of the automation system, separate from any processors onboard carriers. A central controller can facilitate traffic direction, scheduling, and task management for carriers. In some embodiments, a central controller can communicate with subsystems in the automation system and wirelessly communicate with carriers. This may also include sending trajectory or navigational information or instructions to carriers and determining which carriers should go where and when. In some embodiments, local processors may be responsible for managing carriers on local track sections, such as managing local queues. These local processors may act as local equivalents to central controllers.

Decision point: Decision points are points on an automation track where different navigational or trajectory decisions may be made for different carriers. A common example includes a fork in a track. One carrier may proceed without turning, while another may slow down and turn. Decision points may include stopping points at instruments, where some carriers may stop, while others may proceed. In some embodiments, deceleration zones ahead of turns may act as decision points, allowing carriers that will be turning to slow down to limit lateral forces, while others may proceed if not turning or if the motion profile for that carrier does not require slowing down. The decisions made at decision points can be made by processors onboard carriers, processors local to the track section, a central processor, or any combination thereof, depending on the embodiment.

Independent carrier: In some embodiments, carriers may be characterized as independently controlled carriers. Independently controlled carriers are carriers with independently controlled trajectories. In some embodiments, independent carriers may be operating at the same time, on the same track, with carriers carrying one or a plurality of combinations of payloads that differ by size, weight, form factor, and/or content. The trajectories of each independently controlled carrier may be limited by a motion profile that includes; maximum jerk, acceleration, direction, and/or speed for the carrier while moving in the automation system. The motion profile can limit or define the trajectory for each carrier independently. In some embodiments, a motion profile can be different for different sections of the automation system (e.g., in straight track sections vs. around curves to account for the added lateral forces while turning), for different carrier states (e.g., an empty carrier may have a different motion profile from a carrier transporting a sample or from a carrier transporting a reagent or other item), and/or for different carriers. In some embodiments, carriers can include onboard propulsion components that allow individual carriers to independently operate responsive to a motion profile or trajectory or destination instructions intended for each separate carrier.

Intelligent carrier/semi-autonomous carriers: In some embodiments, carriers may be characterized as intelligent carriers. An intelligent carrier is a carrier with onboard circuits that participates in motion, routing, or trajectory decisions. An intelligent carrier can include digital processors that execute software instructions to proceed along an automation surface responsive to the instructions or onboard analog circuits that respond to motion input (e.g., line follower circuits). Instructions may include instructions characterizing motion profiles, traffic, or trajectory rules. Some intelligent carriers may also include onboard sensors to assist onboard processors to route the carrier or make decisions responsive to the carrier's environment. Some intelligent carriers may include onboard components, such as motors or magnets, which allow the carrier to move responsive to control of an onboard processor.

In vitro diagnostics (IVD): In vitro diagnostics (IVD) are tests that can detect diseases, conditions, infections, metabolic markers, or quantify various constituents of bodily materials/fluids. These tests are performed in laboratory, hospital, physician office, or other health professional settings, outside the body of a patient. IVD testing generally utilizes medical devices intended to perform diagnoses from assays in a test tube or other sample vessel or, more generally, in a controlled environment outside a living organism. WD includes testing and diagnosis of disease or quantifying various constituents of bodily materials/fluids based on assays performed on patient fluid samples. IVD includes various types of analytical tests and assays related to patient diagnosis and therapy that can be performed by analysis of a liquid sample taken from a patient's bodily fluids, or abscesses. These assays are typically conducted with analyzers into which tubes or vials containing patient samples have been loaded. IVD can refer to any subset of the IVD functionality described herein.

Landmarks: In embodiments where carriers include onboard sensors, optical or other marks in track surfaces or locations viewable/sensible from track surfaces can act as landmarks. Landmarks can convey geographic information to carriers, such as a current location, upcoming stopping location, decision point, turn, acceleration/deceleration points, and the like.

Lab automation system: Lab automation systems include any systems that can automatically (e.g., at the request of an operator or software) shuttle sample vessels or other items within a laboratory environment. With respect to analyzers, an automation system may automatically move vessels or other items to, from, amongst, or between stations in an analyzer. These stations may include, but are not limited to, modular testing stations (e.g., a unit that can specialize in certain types of assays or can otherwise provide testing services to the larger analyzer), sample handling stations, storage stations, or work cells.

Module: A module performs specific task(s) or function(s) within a modular analytical system. Examples of modules may include: a pre-analytic module, which prepares a sample for analytic testing, (e.g., a decapper module, which removes a cap on top of a sample test tube); an analyzer module, which extracts a portion of a sample and performs tests or assays; a post-analytic module, which prepares a sample for storage after analytic testing (e.g., a recapper module, which reseals a sample test tube); or a sample handling module. The function of a sample handling module may include managing sample containers/vessels for the purposes of inventory management, sorting, moving them onto or off of an automation track (which may include an integral conveyance system, moving sample containers/vessels onto or off of a separate laboratory automation track, and moving sample containers/vessels into or out of trays, racks, carriers, pucks, and/or storage locations.

Payload: While exemplary carriers are described with respect to carrying patient samples, in some embodiments, carriers can be used to transport any other reasonable payload across an automation system. This may include fluids, fluid containers, reagents, waste, disposable items, parts, or any other suitable payloads.

Processor: A processor may refer to one or more processors and/or related software and processing circuits. This may include single or multicore processors, single or multiple processors, embedded systems, or distributed processing architectures, as appropriate, for implementing the recited processing function in each embodiment.

Pullouts, sidecars, offshoot paths: These terms may be used to refer to track sections that are off the main portion of a track system. Pullouts or sidecars may include chords, parallel tracks, or other suitable means for separating some carriers from a primary traffic pattern. Pullouts or sidecars may be configured to facilitate physical queues or allow certain carriers to stop or slow down without disrupting traffic on a main track section.

Samples: Samples refers to fluid or other samples taken from a patient (human or animal) and may include blood, urine, hematocrit, amniotic fluid, or any other fluid suitable for performing assays or tests upon. Samples may sometimes refer to calibration fluids or other fluids used to assist an analyzer in processing other patient samples.

STAT (short turnaround time) sample: Samples may have different priority assigned by a laboratory information system (LIS) or operator to assign STAT priority to samples that should take precedent over non-STAT samples in the analyzer. When used judiciously, this may allow certain samples to move through the testing process faster than other samples, allowing physicians or other practitioners to receive testing results quickly.

Station: A station includes a portion of a module that performs a specific task within a module. For example, the pipetting station associated with an analyzer module may be used to pipette sample fluid out of sample containers/vessels being carried by carriers on an integrated conveyance system or a laboratory automation system. Each module can include one or more stations that add functionality to a module.

Station/module: A station includes a portion of an analyzer that performs a specific task within an analyzer. For example, a capper/decapper station may remove and replace caps from sample vessels; a testing station can extract a portion of a sample and perform tests or assays; a sample handling station can manage sample vessels, moving them onto or off of an automation track, and moving sample vessels into or out of storage locations or trays. Stations may be modular, allowing stations to be added to a larger analyzer. Each module can include one or more stations that add functionality to an analyzer, which may be comprised of one or more modules. In some embodiments, modules may include portions of, or be separate from, an automation system that may link a plurality of modules and/or stations. Stations may include one or more instruments for performing a specific task (e.g., a pipette is an instrument that may be used at an immunoassay station to interact with samples on an automation track). Except where noted otherwise, the concepts of module and station may be referred to interchangeably.

Tubes/sample vessels/fluid containers: Samples may be carried in vessels, such as test tubes or other suitable vessels, to allow carriers to transport samples without contaminating the carrier surfaces.

Exemplary Embodiments

One or more of the problems commonly associated with handling samples of differing priority, such as STAT and normal priority samples. Sample queues typically are needed when there exists an interaction bottleneck at each station. For example, queues may be formed be the competition for a single resource between samples, such as the competition among samples to access a pipette, decapper, robotic handling arm or other instrument that can only interact with a single sample at a time. Typically this results in a several samples that must be physically stopped and temporarily stored while waiting their turn to interact with the instrument. Each sample waits to be processed one at a time at a single interaction point. This can be acceptable when samples are all treated with the same priority. However, when some samples have higher priority, such as patient samples designated as STAT, waiting through a queue may not be acceptable to meet performance goals for handling higher priority samples.

There are two common ways to grant priority access to higher priority samples. If a queue is configured as a FIFO queue (e.g., a buffer on a linear track awaiting access to an instrument), the queue can be flushed. This creates a clear path between the high priority sample and the interaction point on the automation track. In some configurations, the sample currently at the interaction point can complete processing before flushing the queue if it has already started processing, allowing a smooth flushing action where only unprocessed samples need to be flushed and returned later to the queue by circulating the automation track. Another way a priority sample can be processed before other lower priority samples in a queue is to use a mechanism that facilitates random access, such as a carousel. These types of queues and the ways that they can be used to handle STAT samples are described with respect to FIGS. 1 and 2.

The common prior art approaches to granting order-of-processing priority to STAT samples focus on ways to get a STAT sample to the single interaction point before the other, lower-priority samples. Some embodiments of the present invention can take advantage of these techniques, as well. However, some embodiments also approach this problem from another angle by creating a second interaction point to provide access to STAT samples without requiring the STAT sample be given priority access to the interaction point used by the lower priority samples. By utilizing two interaction points, STAT samples can be placed at a location that is not blocked by a queue and be processed without disturbing the existing queue. Instead, an instrument, such a pipette can preserve the lower priority queue and simply spend the next operation cycle for the instrument aspirating a portion of a priority sample from the second interaction point.

In some embodiments, this concept of utilizing a second, priority access point for an instrument can allow a system to utilize a sidecar for normal priority samples, while accessing priority samples that have temporarily stopped on a track portion that is typically used for through traffic of samples, such as a main track portion. In some embodiments, an automation system can include a main traffic loop that provides generally high-speed transit to samples, while queues used for normal priority samples are placed on sidecars or similar structures disclosed herein. This architecture may be useful to allow traffic not related to a queue to generally be unaffected by a delay caused by a queue. In some embodiments, the additional interaction point for high priority samples can be on the main track, allowing a STAT sample to bypass local side cars and the local delays associated with queues thereon. In situations where the number of higher priority STAT samples is low relative to the total number of samples in an automation system, temporarily halting a STAT sample on a main track may be an efficient way to give priority access to STAT samples without generally disrupting overall traffic in the automation system or creating queues on the main track portion as samples (such as other STAT samples) accumulate behind a STAT sample. Exemplary ways in which multiple access points can be created are discussed throughout and may include those shown in FIGS. 9-11.

There are two traditional types of queues. These queues are traditionally physical, but these queues may be implemented logically for use with some embodiments. A first type of queue is a FIFO queue. A FIFO queue is most suitably used by processing modules that perform preprocessing or post-processing tasks (such as a capper or decapper), but may also be used for processing tasks that can tolerate a fixed order of samples (e.g., tests where a single aspiration will be performed). A station utilizing a FIFO queue should be able to operate while the order of samples and timing at which samples will reach the head of the queue are fixed once a sample has been placed in the FIFO queue.

A random-access queue, on the other hand, allows a station to request samples out of order within the queue. Without some knowledge of the order in which a station plans on handling samples in its queue, it may be impossible to predict when a sample will be needed by the station. A sample within a random-access queue may be requested multiple times. Ideally, once a sample is placed in a random-access queue, the station utilizing the queue assumes that it can access the sample at any time, accessing samples in any order, as often and frequent as it likes, and maintains control of each sample in the queue until a sample is explicitly released by that station. Traditional physical random-access queues have utilized carousels to ensure that each sample remains in the queue for random-access and allows samples to be accessed in any order. Traditional physical random-access queues suffer from space constraints, as the size of a carousel will grow in proportion to the square of the number of samples, requiring a large amount of area for a moderate number of samples. Similarly, as the size of a queue rows, the larger carousel may need to move faster to accommodate the large number of samples that may need to be cycled through to provide random-access.

Accordingly, traditional random-access queues have been limited to only a few samples or have limited the extent to which samples may be randomly accessed. For example, in a pure random-access queue, any sample in the queue can be accessed at any time, providing no correlation between the current sample requested and the previous sample. A physical random-access queue may have the following disadvantages: it may increase complexity/cost and reduces reliability; it may increase the steady-state processing time, because the sample must be transferred into and out of the random-access queue (processing delays are implementation dependent); it may increase the physical footprint of the track (e.g., the diameter of the carousel will increase with the number of samples it is designed to hold); it may prevent the queue from being quickly flushed if the module goes offline, in most implementations.

FIG. 1 illustrates a FIFO queue in action. FIFO queue 10 is placed on a sidecar off of the main track 12. Samples moving along main track 12 move in the direction of the arrow. In situation 8, three samples, A, B, and C, are in FIFO queue 10. Sample A is at the head of the queue and is being processed by preprocessing module 14. Module 14 may be a station, such as a decapper, that processes samples in the order in which they arrive. Meanwhile, STAT sample 16 arrives along main track 12 and enters FIFO queue 10. In situation 18, FIFO queue 10 is flushed. While sample A has finished processing, samples B and C must be flushed to expedite the processing of STAT sample 16. Samples B and C must then traverse the entire automation system or a loop within the automation system to be placed back into FIFO queue 10. Meanwhile, sample D arrives along track 12 to be placed into FIFO queue 10. Depending on the requirements of preprocessing module 14, the original order may have significance, in which case samples B and C must make another circuit of the automation system before entering the FIFO queue. In some embodiments, preprocessing module 14 can accommodate the change in the order of the FIFO queue, allowing sample D to be placed in the queue behind the STAT sample 16, which will enable sample D to be processed before samples B and C.

FIG. 2 illustrates a random-access queue in action. Random-access queue 22 is a physical random-access queue that includes four positions in a carousel. Module 24 is given access to samples in the queue by rotating the carousel so that the desired position aligns with a pipette in module 24. Samples travel along main track 12 in the direction of the arrow, and samples to be processed by module 24 are directed into a sidecar that places samples into the random-access carousel. Module 24 may be, for example, an analyzer testing station. In situation 26, samples A, B, and C are placed in the random-access carousel 22. Meanwhile, a STAT sample 16 arrives along main track 12 to be processed by module 24. In situation 27, module 24 completes processing of sample A, while placing STAT sample 16 into an empty slot in the carousel. Sample D arrives along main track 12 for processing. In situation 28, sample A completes processing allowing another sample to move to the head of the queue for processing by module 24. In this instance, the STAT sample is given priority. Carousel 22 moves the STAT sample into position for interaction with module 24. Sample D may be placed into the empty slot left by sample A. It should be noted that in this situation, samples B and C are not flushed, because STAT sample 16 can be accommodated by the carousel and be moved to allow the STAT sample to be processed before samples B and C. Furthermore, because samples B and C remain resident in the random-access queue, module 24 can decide whether to process samples B and C ahead of sample D, depending on the local scheduling algorithms used by module 24 to facilitate tests on the samples.

Embodiments of the present invention may utilize queues having any subset of the functionality of the queues illustrated in FIGS. 1 and 2 by decoupling physical queues from logical queues. Some embodiments of the present invention include systems and methods that provide a more efficient lab automation system to allow samples to be shuttled between and amongst various analyzer testing stations with less latency and more individual control. Some embodiments of the present invention can reduce or eliminate some queues experienced by samples traversing the automation system. Some embodiments utilize the techniques discussed herein to limit delays due to singulation points or other delays that cause unwanted traffic stoppage on main transit portions of the automation track, such as a main loop that links sidecars for a plurality of modules.

Exemplary Analyzers

Usually, samples need to undergo many different types of testing in an automated clinical analyzer (analyzer), which may not be available in a single testing station. Testing stations within an analyzer can be adapted for specialized testing. For example, immunoassays may be performed by an immunoassay station that includes certain incubation capabilities and uses specific reagents that are unique to immunoassays. Chemical analysis can be performed by a clinical analyzer and electrolyte chemistry analysis can be conducted by an ion-selective electrode (ISE) clinical analyzer. By using this modular approach, an analyzer can be adapted not only to the types of testing being done on samples, but also the frequency and volume of testing necessary to accommodate the needs of the lab. If additional immunoassay capability is needed, a lab may choose to add additional immunoassay stations and increase overall throughput for immunoassay testing in their system.

An exemplary track geometry, for use in transporting samples within an analyzer typical in prior art configurations, is shown in FIG. 3. A similar geometry may be used in some embodiments of the present invention, as well. This track can include prior art friction tracks, which may introduce problems in designing a track system. However, certain embodiments of the present invention could also use a similar geometry without necessarily employing a friction track for motion. Track 100 can be a generally oval-shaped track that conveys samples in pucks or trays between various stations, such as sample preparation or analyzing/testing stations 110, 120, and 130. Track 100 could be a single direction track or, in some instances, a linear bidirectional track. In this exemplary set-up, each analyzer 110, 120, 130 is serviced by a respective sidecar 112, 122, 132. At the junction between the track 100 and each sidecar, a gate or switch can be placed that allows samples to be diverted to or from track 100 to the sidecar. The oval nature of track 100 can be used to circulate samples while they wait for access to each analyzer. For example, analyzer 110 may have a full queue in sidecar 112, such that new samples on track 100 cannot be diverted to pullout 112 until analyzer 110 finishes handling a pending sample in sidecar 112 and inserts it back into the main traffic flow of track 100.

In some prior art systems, each sidecar can be serviced by a handling mechanism such as sample probe arms 114, 124, and 134. These robotic handling arms can aspirate sample material from samples in a sidecar via a probe needle, or can pick up a sample tube from the sidecar and transport it into the corresponding testing station. In this exemplary system, the available testing stations include an immunoassay station 110, a low-volume chemistry station 120, and an expandable dilution/ISE electrolyte and high-volume chemistry station (or stations) 130. Some advantages of this approach are that the track 100 can be part of a separate lab automation system that can be added onto otherwise self-contained stations, and the track 100 and stations 110, 120, and 130 can be independently upgraded, purchased, or serviced. Some stations, such as high-volume chemistry station 130, can include their own friction track 136 that operates independently of track 100. Friction track 136 can include a bidirectional friction track that allows samples to move between sub-modules of high-volume chemistry station 130. A drawback of this type of system is that the separate friction tracks operate independently and, control of overall automation becomes more complicated. Furthermore, transitions between friction tracks 136 and 100 can be slow and cumbersome, particularly where there is no direct route between two friction tracks. In some systems, moving between tracks may require lifting and placing samples via a robot arm.

Prior art lab automation systems for analyzers generally treat individual analyzer/testing stations as generic destinations for a sample on the track. In some embodiments of the present invention, the lab automation system can be integrated within the individual testing stations, which can substantially reduce or eliminate the complexity of the individual testing stations and reduce the need for separate sample handling systems within each station. In some embodiments, by integrating the lab automation system into the stations, the system can begin to treat individual stations less as generic destinations and more as portions of a multi-route track onto which a sample can travel.

Figure 4A:
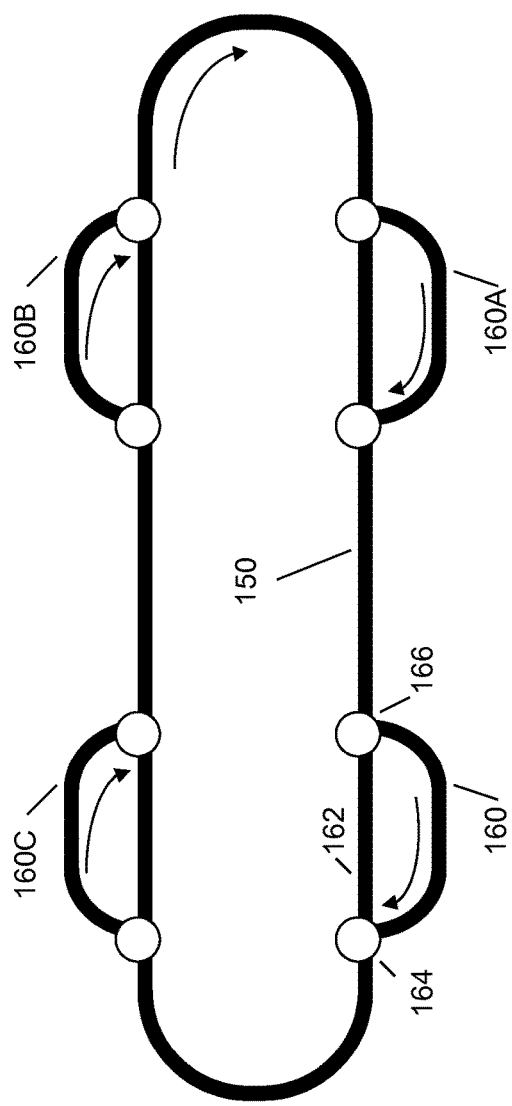
FIGS. 4A and 4B are diagrammatic views of track geometries that can be used with the automation system embodiments disclosed herein.

FIG. 4A shows one embodiment of a track system that can be adapted for use with some embodiments. Track 150 is a rectangular/oval/circular track on which sample carriers move in a clockwise (or counterclockwise) direction. Track 150 may be unidirectional or bidirectional. Carriers can transport any suitable payload with the IVD environment, such as fluid samples, reagents, or waste. Fluids, such as patient samples can be placed in a container or vessel, such as a test tube, vial, cuvette, etc. that can be transported by a carrier. Carriers, and by extension payloads such as samples, can move on the main track 150 or be diverted via decision points such as 164 or 166. These decision points can be mechanical gates (as in the prior art) or other mechanisms suitable for allowing a sample to be diverted from the main track 150 to a sidecar, such as 160, 160A, 160B, 160C as described herein. By way of example, if a sample carrier is traversing the main path 150 and reaches decision point 166, it can be made to continue on the main track to segment 162 or it can be made to divert to sidecar 160. The systems and methods by which the decision can be made to divert the sample carrier at decision point 166 are described throughout.

Figure 4B:
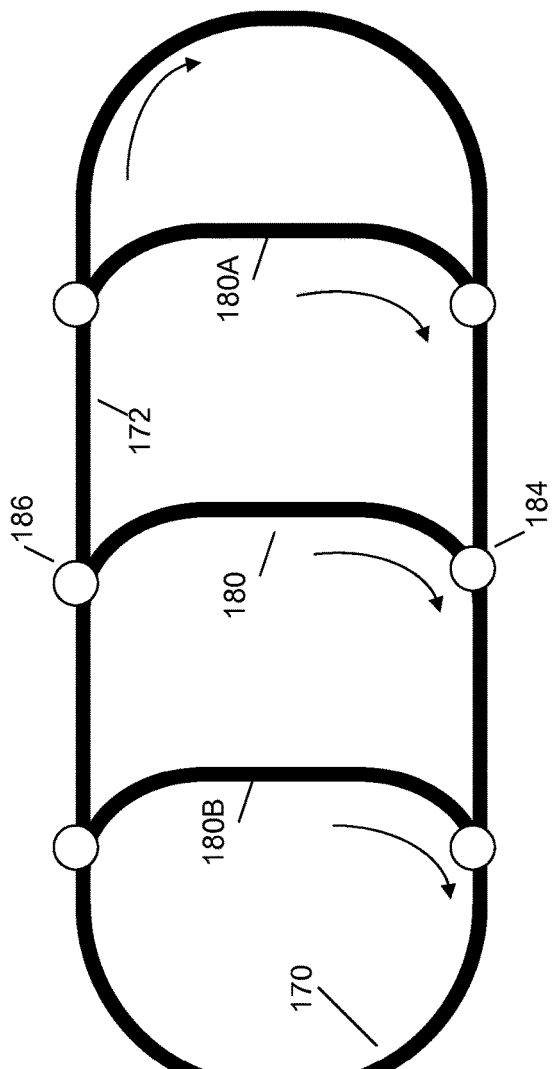

FIG. 4B shows an alternative track layout that may be suitable for certain embodiments. Track 170 is also a generally circular track with sample carriers moving clockwise (or counterclockwise). In this example, rather than having sidecars outside of the track, pullouts 180, 180A, and 180B are chords within the track. Similarly, when sample carriers reach decision points, they may be diverted off of the main path to a side path, such as path 180. At decision point 186, a sample on the main track 170 can be made to continue on the main track or be diverted onto path 180. Once an analyzer station along handling path 180 is done processing the sample, the sample proceeds to decision point 184 where it may be placed back onto the main path 170.

Figure 5:
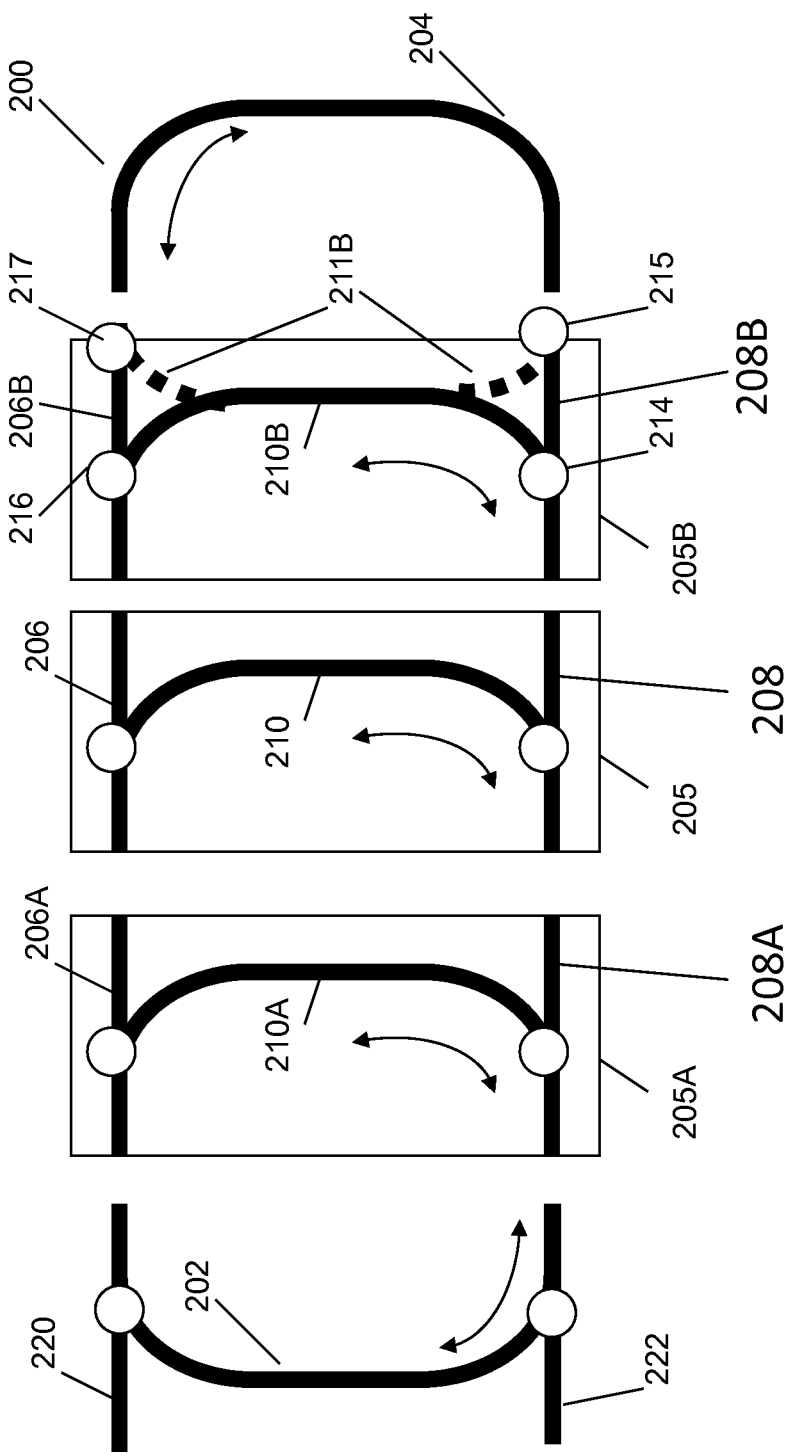
FIG. 5 is a diagrammatic view of an exemplary modular track configuration that can be used with the embodiments disclosed herein.

FIG. 5 shows a modular approach to the automation system track that can be used for certain embodiments of the present invention. In this example, the tracks may be integrated into individual analyzer stations, such that the track can be used as part of the internal motion or sample handling system of individual lab stations. In the prior art, it is common to have multiple different types of motion systems within different analyzer/testing stations. For example, some stations can include friction tracks for shuttling pucks or trays of sample tubes, and may include carousels containing smaller vessels, such as cuvettes and reaction vessels, into which portions of the sample can be aspirated and dispensed. In some embodiments, by integrating portions of the track system into the analyzer stations themselves, each station can include its own queuing logic and may be simplified to eliminate unnecessary internal motion systems.

With respect to FIG. 3, the track 200 can be broken into modular components that are integrated into analyzer modules. In this exemplary track, modules 205, 205A, and 205B can be combined with one another and optionally other modular track components 202 and 204 to form a track similar to that shown in FIG. 4B. For instance, 205A can be a module that performs the same function as immunoassay 110 (FIG. 3), 205 can be a module that performs the same function as low-volume chemistry module 120 (FIG. 3), and 205B can be a module that performs ISE electrolyte testing, like module 130 (FIG. 3). In this example, the main outer track can be formed by track segments 202, 204, 206, 206A, 206B, 208, 208A, and 208B. Within the analyzer modules 205, 205A, and 205B, internal paths 210, 210A, and 210B form pullouts from the main track. The internal paths can be used for internal queuing and can be managed independently within each analyzer module to allow each module to have greater control over samples to be processed.

One advantage of integrating track 200 and sub-paths 210, 210A, and 210B into the analyzer modules 205, 205A, and 205B, respectively, is that the internal handling mechanisms within each analyzer module can be specially adapted to better coordinate with the track sub-paths. In some embodiments, modules 205, 205A, and 205B can be adapted to process each sample within a period that is less than an operation cycle of the overall analyzer, leaving enough time for the sample to be routed along the track system to another module after processing, allowing the other module to immediately process the sample on the next operation cycle. As used herein, an operation cycle is a unit of time used by scheduling algorithms to allot processing time to modules for sample assays. These can be dynamic or fixed and can allow synchronous operation of the modules in the analyzer and provide a reliable timing model for scheduling samples amongst multiple modules in the analyzer. The operation cycle time can be chosen to be the time needed by any given module between when it starts processing a first sample, and when it is ready to process another sample under expected steady-state conditions. For example, if an analyzer can process one test every three seconds, and the expected average tests per sample is seven, the operation cycle time can be 21 seconds. It should be understood that individual modules can implement efficiency techniques, such as parallelism or processing multiple samples within a cycle, to maximize throughput, even when the number of tests-per-sample varies from an expected amount. Furthermore, it should be understood that in some embodiments, individual modules have different operation cycle times, and these modules can operate substantially asynchronously from one another. Virtual queues or buffers can be used to assist the management of sample scheduling where cycle times or demand vary between modules.

Enabling transit between modules in the analyzer in a reliable time frame, on the order of a single operation cycle or less, achieves many performance advantages not possible with prior art track systems. If a sample can be reliably handled by an analyzer module and transported to the next analyzer module within a single cycle of the analyzer, traffic handling in queuing becomes much simpler, throughput becomes more consistent, and latency can be controlled and reduced. Essentially, in such an analyzer, a sample can reliably be handled by the track system and processed uniformly such that a sample does not sit idly on the track system waiting in queues. Furthermore, queues within the system, such as queues within a given analyzer module, can reliably be shortened, limited by the number of modules within the system.

In some embodiments of the present invention, the reliable and rapid nature of the track system enables queues to be virtual, rather than physical. A virtual queue can be handled in software, rather than by physical limitations. Traditionally, queues have been physical. The simplest physical queue is effectively a traffic jam at any given part of a sample handling operation. A bottleneck creates a first-in first-out (FIFO) queue, where sample carriers are effectively stopped in a line, providing a buffer so that an analyzer or a decision point can request the next sample in the queue when it is ready. Most prior art lab automation tracks maintain FIFO processing queues to buffer samples that are waiting to be processed by the attached modules (analyzers or pre/post analytic devices). These buffers allow the track to process sample tubes at a constant rate, even though the modules or operator requests can create bursts of demand. FIFO queues can also substantially increase the throughput of the individual modules by allowing them to perform preprocessing tasks for future samples, for example, prepare a cuvette or aspirate reagent, while processing the current sample. While the rigid predictability of FIFO queues enables the parallelization of some processing tasks, it also can prevent the modules from using opportunistic scheduling that may increase throughput by reordering tests on samples to optimize resources. For example, the internal resource conflicts of most immunoassay analyzers can be so complex that the analyzers need to interleave the tests from multiple samples in order to reach maximum efficiency. A FIFO queue can reduce the throughput of these analyzers by as much as 20%. Another challenge with FIFO queues is their inability to handle priority samples (e.g., a STAT sample). If a STAT sample needs to be processed immediately, the entire FIFO queue has to be flushed back onto the main track, delaying all other samples on the main track and forcing the original module to slowly rebuild its queue.

Another type of queue is a random-access (RA) queue. A carousel is an example of a physical RA queue found in analyzer modules. By aliquoting a portion of a sample into one or more vessels in a carousel ring, an analyzer module can select any of a number of samples to process at any time within the analyzer. However, carousels have many drawbacks, including added complexity, size, and cost. A carousel also increases the steady-state processing time, because a sample must be transferred into and out of the random-access queue. Processing delays depend on the implementation, such as the number of positions in a carousel. On the other hand, by having random-access to samples, a local scheduling mechanism within a module can process samples in parallel, performing sub-steps in any order it desires.

In some embodiments, carousels or other RA queues can be eliminated from the modules and the sub-paths (e.g., 210) from the automation system can be used as part of an RA or FIFO queue. That is, if the travel time for a sample between any two points can be bounded to a known time that is similar to that of a carousel, (such as predictably less than a portion of an operation cycle), the track 200 can be part of the queue for a given module. For example, rather than using a carousel, module 205 can utilize samples in carriers on sub-path 210. Preprocessing steps, such as reagent preparation, can be conducted prior to the arrival of a sample under test. Once that sample under test arrives, one or more portions of the sample can be aspirated into cuvettes or other reaction vessels for an assay. In some embodiments, these reaction vessels can be contained within module 205, off track, while in other embodiments, these reaction vessels can be placed in carriers on sub-path 210 to allow easy motion. If the sample under test is required to be at a module for longer than an operation cycle, or if multiple samples will be processed by the module during an operation cycle, the sub-path 210 can act as a queue for the module.

Furthermore, samples not yet under test, which may be currently located at other modules, can be scheduled for the next operation cycle. These next-cycle samples can be considered as residing in a virtual queue for module 205. A module can schedule samples to arrive during a given operation cycle for any sample on track 200. A central controller, or controllers associated with modules themselves, can resolve any conflicts over a sample for a given cycle. By giving a module prior knowledge of the arrival time of a sample, each module can prepare resources and interleave tests or portions of tests to more efficiently allot internal resources. In this manner, modules can operate on samples in a just-in-time manner, rather than by using large physical buffers. The effect is that the virtual queue for a given module can be much larger than the physical capacity of the sub-path serving that module, and existing scheduling algorithms can be used. Effectively, each module can treat track 200 as it would treat a sample carousel in a prior art module.

If decision points such as 214 and 216 can be streamlined such that there is no need for a queue at each decision point, the only physical queues can be within sub-paths 210, 210A, and 210B. As described above, these can be treated as RA queues or FIFO queues. If a STAT sample is placed onto track 200, RA queues within sub-paths 210, 210A, and 210B need not be flushed, as the STAT sample can be processed immediately. Any FIFO queues can be individually flushed. For example, if a STAT sample is placed onto track 200 at section 222, the sample may be routed to the appropriate analyzer 205B via the outside track and decision point 216. If there are other samples (and by extension the sample carriers transporting those samples) waiting in the queue in path 210B, only those samples in the queue may need to be flushed to allow a STAT sample to take priority. If the outer track 200 is presumed to take less than an operation cycle to traverse, any samples that were flushed from the queue in 210B can simply be circulated around the track and placed immediately back into the queue in path 210B immediately behind the STAT sample, eliminating any down time caused by the STAT sample. However, it may still be desirable to utilize a separate location for some instruments to access STAT samples, as discussed throughout.

Furthermore, it may be desirable to provide separate entry paths for STAT samples to place them into the automation system sooner. Entry paths 220 and 222 can be used to input samples to the track 200. For example, regular priority samples can be placed onto track 200 at input 220 and STAT priority samples can be placed on input 222. These inputs can be used as outputs for samples when complete, or other ports (not shown) can be used as the output paths for used samples. Input 220 can be implemented as an input buffer, acting as a FIFO queue for input samples seeking access to the track 200. Once a sample reaches the head of the queue at input 220, it can be moved onto the track (either by being placed in a carrier or by being placed in a carrier when it is placed in input 220). A STAT sample can enter the track 200 immediately after being placed at input 222 or, if track 200 is overcrowded, the STAT sample can enter the track at the next available uncrowded operation cycle. Some embodiments monitor the number of carriers on the track during an operation cycle and limit the total number to a manageable amount, leaving the remainder in input queues. By restricting samples at the input, track 200 can be free of traffic, allowing it to always be operated in the most efficient manner possible. In these embodiments, the transit time of a sample between two modules can be a bounded value (e.g., less than some portion of an operation cycle), allowing simplified scheduling.

In some embodiments, the track system 200 can be designed to be bidirectional. This means that sample carriers can traverse the outside path and/or any sub-paths in either direction. In some embodiments, additional sub-paths, such as 211B accessed via additional decision points 215 and 217, can assist in providing bidirectional access. Bidirectional paths can have inherent advantages. For example, if normal priority samples are always handled in the same direction, a STAT sample can be handled in the opposite direction along the sub-path. This means that a STAT sample can essentially enter the exit of the sub-path and be immediately placed at the head of the queue without requiring the queue to be flushed. For example, if a STAT sample is placed on track 200 at segment 204, it can enter path 210B via decision point 214 and proceed into path 210B to be immediately placed at the head of any queue. Meanwhile, in all of these examples, because queues are presumed to be limited generally to sub-paths, there is no need to flush queues in other modules if a STAT sample does not need immediate access to those modules. Any additional modules that need to service a STAT sample on a subsequent cycle can flush their queues at that point, providing just-in-time access to a STAT sample without otherwise disrupting the operation of each analyzer module.

Modular design also allows certain other advantages. If the automation systems within an analyzer module are adapted to take advantage of the track system contained in the module, new features can be added that use the common track. For example, a module could have its own internal reagent carousel that includes all of the reagents necessary for performing the assays prescribed for the samples. When reagents stocked in the analyzer module run low, an operator can replenish the reagents in some embodiments by simply loading additional reagents onto carriers on the track 200. When the reagents on track 200 reach the appropriate module, the module can utilize mechanical systems such as an arm or a feeder system that takes the reagents off of the track and places the reagents in the reagents store for the module.

In some embodiments, the individual track portions shown in FIG. 5 and FIG. 4A and FIG. 4B can be operated independently from one another, or can be passive. Independent carrier movement provides advantages over friction-based track systems, such as non-localized conveyor belts where the entire friction track must be moved to effect movement of a sample carrier. This means that other samples also on that track must move at the same rate. This also means that if certain sections operate at different speeds, collisions between passive carriers carrying samples can occur.

FIG. 6A depicts an exemplary carrier 250 for use with some embodiments of the present invention. Carrier 250 can hold different payloads in different embodiments. One payload can be a sample tube 255, which contains a fluid sample 256, such as blood or urine. Other payloads may include racks of tubes or reagent cartridges or any other suitable cartridge. Sample carrier 250 includes a main body 260, which can house the internal electronic components describe herein. The main body 260 supports a bracket 262, which can accept a payload. In some embodiments, this is a shallow hole that is designed to accept a fluid container 255, such as a sample tube, and hold it with a friction fit. In some embodiments, the friction fit can be made using an elastic bore or a clamp that can be fixed or energized with a spring to create a holding force. In some embodiments, sample racks and reagent cartridges can be designed to also attach to the bracket 262, allowing bracket 262 to act as a universal base for multiple payload types.

Body 260 can include or be coupled to guide portion 266, which allows the carrier 250 to follow a track between decision points. Guide portion 266 can include, for example, a slot to accept one or more rails in the track, providing lateral and/or vertical support. In some embodiments, the guide portion allows the carrier 250 to be guided by walls in the track, such as the walls of a trough-shaped track. The guide portion 266 can also include drive mechanisms, such as friction wheels that allow a motor in the carrier body 260 to drive the carrier or puck 250 forward or backward on the track. The guide portion 266 can include other drive components suitable for use with the embodiments described throughout, such as magnets or induction coils.

Rewritable display 268 can be provided on the top of the carrier 250. This display can include an LCD oriented panel and can be updated in real time by the carrier 250 to display status information about sample 256. By providing the electronically rewritable display on the top of the carrier 250, the status information can be viewed at a glance by an operator. This can allow an operator to quickly determine which sample he/she is looking for when there are multiple carriers 250 in a group. By placing the rewritable display on top of the carrier 250, an operator can determine status information even when multiple carriers 250 are in a drawer or rack.

Figure 6B:
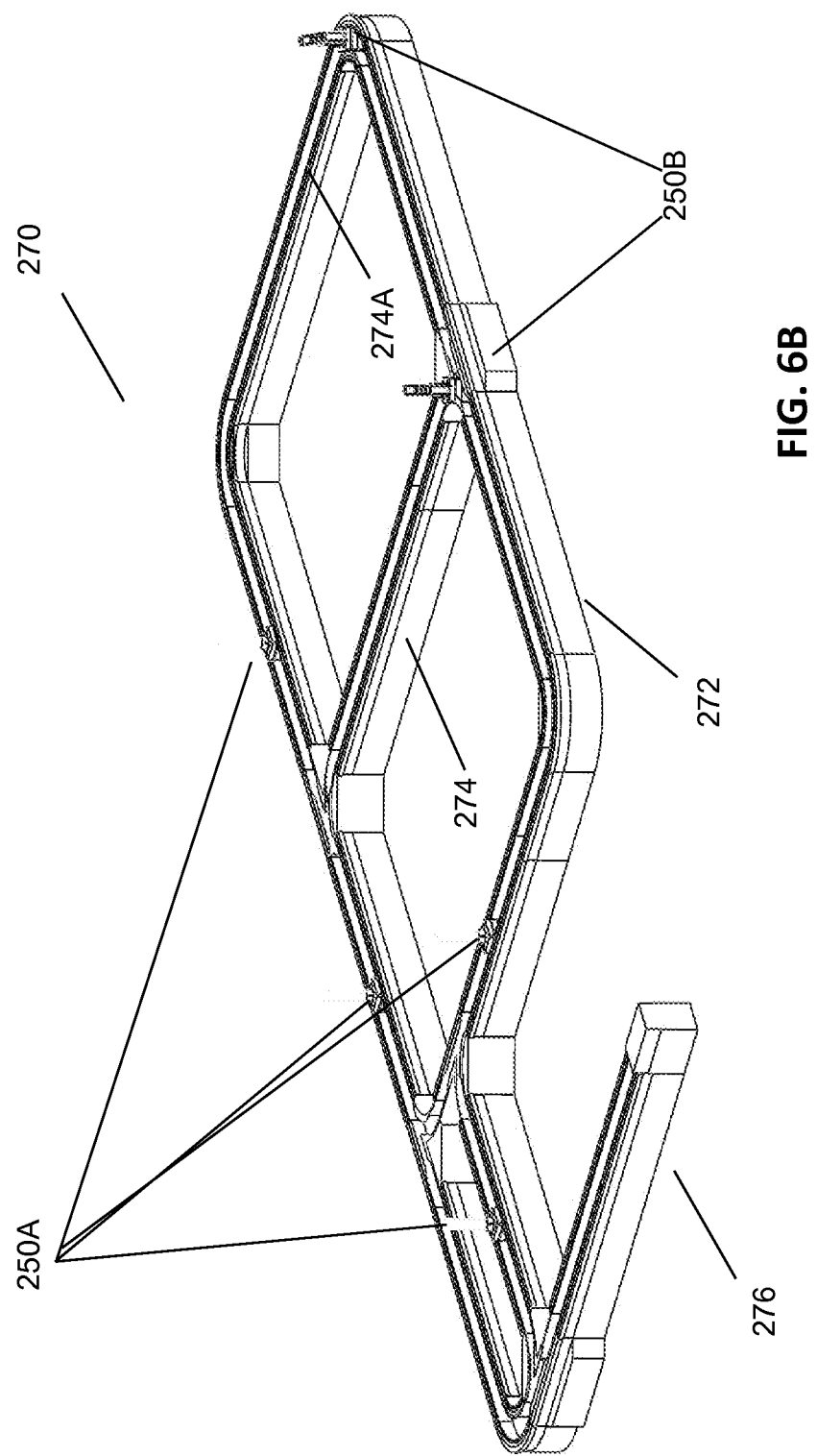
FIG. 6B is a perspective view of an exemplary track configuration that can be used with the embodiments disclosed herein.

FIG. 6B shows an exemplary track configuration 270 for use by carriers 250. In this example, carriers 250A transport sample tubes, while carriers 250B transport racks of tubes along main track 272 and/or subpaths 274 and 274A. Path 276 can be used by an operator to place samples into carriers or remove samples from these carriers.

Figure 6C:
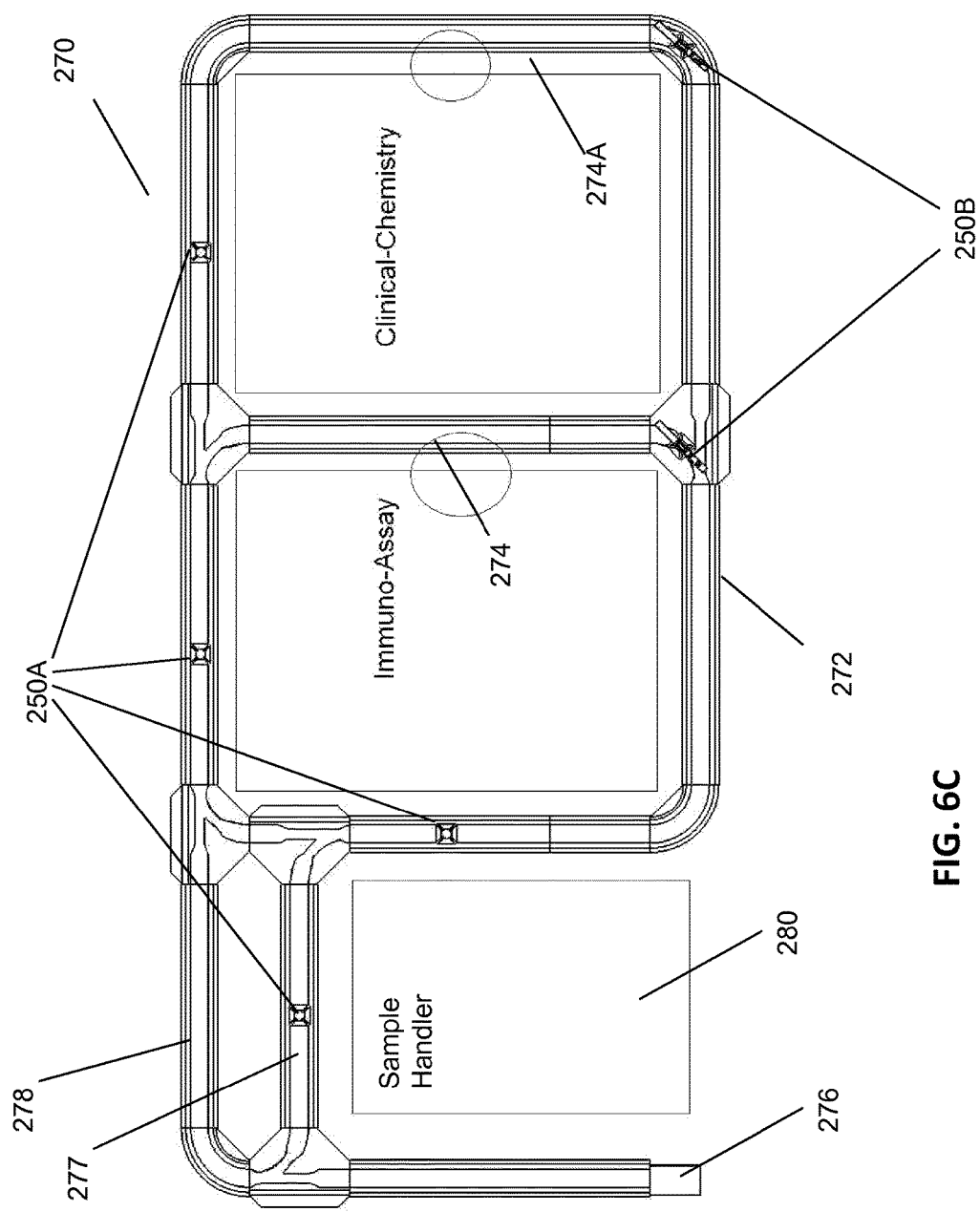
FIG. 6C is a top view of an exemplary automation systems that can be used with the embodiments disclosed herein.

FIG. 6C shows an additional view of an exemplary track configuration 270. In this example, sub-path 274 serves an immunoassay station, while subpath 274A serves a clinical chemistry station. Input/output lane 276 can be served by a sample handler station 280 that uses subpaths 277 and 278 to buffer samples for insertion or removal of the samples from the main track 272.

In some embodiments, the sample handler 280 can also load and unload samples or other payloads to/from the carriers 250A and 250B. This allows the number of carriers to be reduced to the amount needed to support payloads that are currently being used by the stations in track system 270, rather than having a vast majority of carriers sitting idle on tracks 277 and 278 during peak demand for the analyzer. Instead, sample trays (without the carriers disclosed herein) can be placed/removed by an operator at input/output lane 276. This can reduce the overall cost of the system and the number of carriers needed can be determined by the throughput of the analyzer, rather than based on anticipating the peak demand for the analyzer in excess of throughput.

Intelligent Carriers

Some embodiments of the present invention can utilize intelligent independent carriers to enable certain improvements over passive pucks on friction-based tracks. For example, one disadvantage of prior art track systems is that at each decision point the decision for directing a puck is made by the track by rotating the puck and reading a barcode optically. Rotating and optical reading is a relatively slow process. Furthermore, this process can be redundant because the system has knowledge of the identification of the sample tube when the sample tube is placed into the puck by an operator. Embodiments of the present invention can include carriers that have means to identify the contents of the sample tube (and optionally communicate this information to the automation system) without requiring the carrier to be stopped, rotated, and read optically. By reducing or removing singulation points from the main track portions, STAT samples can be further expedited by allowing samples on the main track portions to freely move between modules.

For example, a carrier can include an onboard optical reader to automatically read a barcode of a payload. The results of the scan can then be stored in the memory of a carrier if the carrier has onboard processing capability. Alternatively, an outside source, such as a hand barcode reader operated by an operator at the time of placing the sample into the carrier, can communicate the barcode information of the payload to the carrier via RF signal or other known means, such as communication protocol using temporary electrical contact or optical communication. In some embodiments, the association of the carrier with the payload can be stored external to the carrier and the identity of the carrier can be conveyed by the carrier to the system by RF, optical, or near field communication, allowing the system to assist in routing or tracking the carrier and the payload. Routing decisions can then be made by the carrier or by identifying the carrier, rather than reading a unique barcode of a payload.

By moving processing capability and/or sensor capability onto each individual carrier, the carriers can participate actively and intelligently in their own routing through the track system. For example, if individual carriers can move independently of one another either by autonomous motive capabilities or by communication with the track, certain performance advantages can be realized.

By allowing carriers to move independently, carriers can move around the track faster. One key limitation on the motion of a carrier is that it should not spill an open-tube sample. The limiting factor is generally not the velocity of the carrier in a straight line, but the acceleration and jerk experienced by the carrier (while speeding up, slowing down, or turning), which may cause splashing. For prior-art friction-based track systems, the velocity of the track is typically limited to prevent acceleration and jerk experienced by pucks from exceeding threshold amounts because the entire track moves. However, by using a track system with independently operating sections that can respond to individual carriers, or individual carriers that have independent motive capability, the acceleration of any given carrier can be tailored to limit acceleration/deceleration and jerk, while allowing the average velocity to be greater than that of traditional tracks. By not limiting the top speed of a carrier, the carrier can continue to accelerate on each track section as appropriate, resulting in a substantially higher average speed around the track. This can assist the carrier in traversing the entire track system in less than one machine cycle of the analyzer. These machine cycles can be, for instance 20 or 40 seconds.

Similarly, an autonomous carrier can know its own identity and that of its payload. This allows the carrier to actively participate or assist in the routing decision process at individual decision points. For example, upon reaching a decision point (e.g., switch, intersection, junction, fork, etc.), a carrier can communicate its identity and/or the identity of its payload to the track or any switching mechanism (or its intended route that the carrier has determined based on the payload identity), via RF or near field communication. In this scenario, the carrier does not need to be stopped at a decision point for a barcode scan. Instead, the carrier can keep going, possibly without even slowing down, and the carrier can be routed in real time. Furthermore, if the carrier knows where it is going or communicates its identity to the track (such that the track knows where the carrier is going) before the carrier physically reaches a decision point, the carrier can be made to decelerate prior to a decision point if the carrier will be turning. On the other hand, if the carrier does not need to turn at the decision point, the carrier can continue at a higher velocity because the sample carried by the carrier will not undergo cornering forces if the carrier is not turning at the decision point or a curved section of the track.

An autonomous carrier can also include onboard processing and sensor capabilities. This can allow a carrier to determine where it is on the track and where it needs to go, rather than being directed by the track (although in some embodiments, a central controller sends routing instructions to the carrier to be carried out). For example, position encoding or markers in the track can be read by the carrier to determine a carrier's location. Absolute position information can be encoded on a track surface to provide reference points to a carrier as it traverses the track. This position encoding can take many forms. The track may be encoded with optical markers that indicate the current section of the track (e.g., like virtual highway signs), or may further include optical encoding of the specific absolute location within that section of track (e.g., like virtual mile markers). Position information can also be encoded with markings between absolute position marks. These can provide synchronization information to assist a carrier in reckoning its current trajectory. The optical encoding scheme may take on any appropriate form known to one skilled in the art. These marks used by the encoding scheme may include binary position encoding, like that found in a rotary encoder, optical landmarks, such as LEDs placed in the track at certain positions, barcodes, QR codes, data matrices, reflective landmarks, or the like. General position information can also be conveyed to the carrier via RF/wireless means. For example, RFID markers in the track can provide near field communication to the carrier to alert the carrier that it has entered a given part of the track. In some embodiments, local transmitters around or near the track can provide GPS-like positioning information to enable the carrier to determine its location. Alternatively, sensors in the track, such as Hall effect sensors or cameras, can determine the position of individual carriers and relay this information to the carrier.

Similarly, the carrier can have sensors that indicate relative motion, which provide data that can be accumulated to determine a position. For example, the carrier may have gyroscopes, accelerometers, or optical sensors that observe speckle patterns as the carrier moves to determine velocity or acceleration, which can be used to extrapolate a relative position.

Because a carrier can know where it is and its motion relative to the track, a carrier can essentially drive itself, provided it knows its destination. The routing of the carrier can be provided in many different ways in various embodiments. In some embodiments, when a carrier is loaded with the sample, the system can tell the carrier the destination analyzer station. This information can be as simple as the identification of the destination station in embodiments where the carrier has autonomous routing capability. This information can also be detailed information such as a routing list that identifies the specific path of the individual track sections and decision points that a carrier will traverse. Routing information can be conveyed to the carrier via any communication method described herein, such as RF communication, near field/inductive communication, electrical contact communication, or optical communication.

In an exemplary embodiment, when an operator scans the barcode of the sample tube and places it in a carrier, the system determines the identity of the carrier and matches it with the identity of the sample. The system then locates the record for the sample to determine which tests the sample must undergo in the analyzer. A scheduler then allocates testing resources to the sample, including choosing which tests will be done by individual testing stations and when the sample should arrive at each testing station for analysis. The system can then communicate this schedule (or part of the schedule) to the carrier to inform the carrier of where it needs to go, and optionally when it needs to go and/or when it needs to arrive.

Once the carrier is placed onto the track system, the routing capabilities and location acquisition systems of the carrier enable the carrier to determine where it is on the track and where it needs to go on the track. As the carrier traverses the track, the carrier reaches individual decision points and can be directed along the main track or along sub-paths as appropriate. Because each carrier operates independently from one another, a carrier can do this quite quickly without necessarily stopping at each decision point and without waiting for other carriers in a queue. Because these carriers move quickly, there is less traffic on the main sections of the track, which reduces the risk of collision or traffic jams at decision points or corners in the track (e.g., sections where carriers might slow down to avoid excessive forces on the sample).

Motive force can be provided to the carriers in many ways. In some embodiments, the track actively participates in providing individualized motive force to each carrier. In some embodiments, motive force is provided by electromagnetic coils in the track that propel one or more magnets in the carrier. An exemplary system for providing this motive force is the track system provided by MagneMotion, Inc., which can generally be understood by the description of the linear synchronous motors (LSMs) found in U.S. Published Patent Application 2010/0236445, assigned to MagneMotion, Inc. These traditional systems utilizing this magnetic motion system have included passive carriers that lack the integrated intelligence of the carriers described herein, and all routing and decisions are made by a central controller with no need for active carriers that participate in the routing and identification process.

In embodiments that utilize magnetic motion, the electromagnetic coils and the magnets operate as an LSM to propel each individual carrier in the direction chosen with precise control of velocity, acceleration, and jerk. Where each coil on the track (or a local set of coils) can be operated independently, this allows highly localized motive force to individual carriers such that individual carriers can move with their own individually tailored accelerations and velocities. Coils local to a carrier at any given moment can be activated to provide precise control of the direction, velocity, acceleration, and jerk of an individual carrier that passes in the vicinity of the coils.

In some embodiments, a track may be comprised of many individually articulable rollers that act as a locally customizable friction track. Because individual micro-sections of the track can be managed independently, rollers immediately around a carrier may be controlled to provide individualized velocity, acceleration, and jerk. In some embodiments, other active track configurations can be used that provide localized individual motive force to each carrier.

In some embodiments, the track may be largely passive, providing a floor, walls, rails, or any other appropriate limitations on the motion of a carrier to guide the carrier along a single dimension. In these embodiments, the motive force is provided by the carrier itself. In some embodiments, each individual carrier has one or more onboard motors that drive wheels to provide self-propelled friction-based motive force between the track and the carrier. Unlike traditional friction tracks, where the track is a conveyor, carriers with driven wheels can traverse the track independently and accelerate/decelerate individually. This allows each carrier to control its velocity, acceleration, and jerk at any given moment to control the forces exerted on its payload, as well as traverse the track along individually tailored routes. In some embodiments, permanent magnets may be provided in the track and electromagnets in the carrier may be operated to propel the carrier forward, thereby acting as an LSM with the carrier providing the driving magnetic force. Other passive track configurations are also contemplated, such as a fluid track that allows carriers to float and move autonomously via water jets or the like, a low friction track that allows carriers to float on pockets of air provided by the track, (e.g., acting like a localized air hockey table), or any other configuration that allows individual carriers to experience individualized motive forces as they traverse the track.

Figure 7:
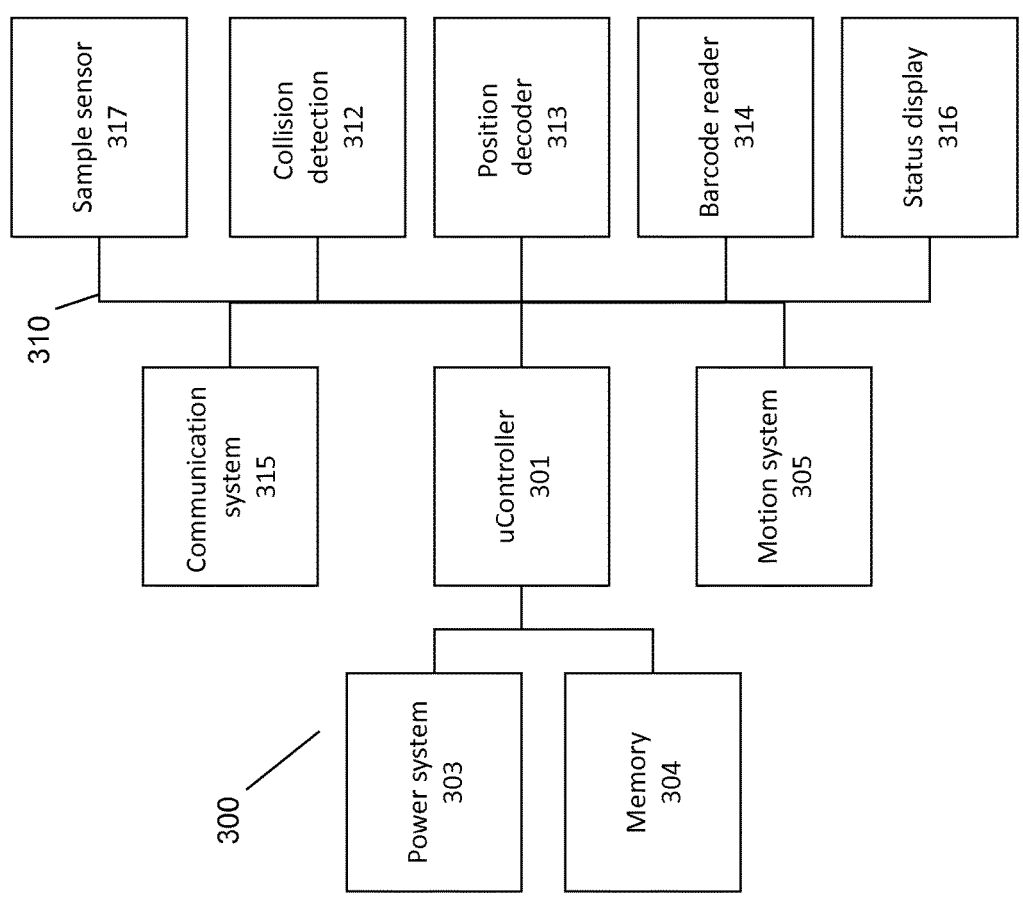
FIG. 7 is a system block diagram of the control systems including onboard active carriers that can be used with certain embodiments disclosed herein.

FIG. 7 shows a top-level system diagram of the control systems and sensors for an exemplary intelligent autonomous carrier 300. Carrier 300 is controlled by a microcontroller 301 that includes sufficient processing power to handle navigation, maintenance, motion, and sensor activities needed to operate the carrier. Because the carrier is active and includes onboard electronics, unlike prior art passive carriers, the carrier includes an onboard power station. The details of this station vary in different embodiments of the present invention. In some embodiments, power system 303 comprises a battery that may be charged as the carrier operates, while in other embodiments, the battery is replaceable or can be manually charged when the carrier is not operating. Power system 303 can include the necessary charging electronics to maintain a battery. In other embodiments, power system 303 comprises a capacitor that may be charged by inductive or electrical contact mechanisms to obtain electrical potential from the track itself, in much the same way a subway car or model train might receive power.

Microcontroller 301 communicates with system memory 304. System memory 304 may include data and instruction memory. Instruction memory in memory 304 includes sufficient programs, applications, or instructions to operate the carrier. This may include navigation procedures as well as sensor handling applications. Data memory in memory 304 can include data about the current position, speed, acceleration, payload contents, navigational plan, identity of the carrier or payload, or other status information. By including onboard memory in carrier 300, the carrier can keep track of its current status and uses information to intelligently route around the track or convey status information to the track or other carriers.

Microcontroller 301 is responsible for operating the motion system 305, sensors 312, 313, and 314, communication system 315, status display 316, and sample sensor 317. These peripherals can be operated by the microcontroller 301 via a bus 310. Bus 310 can be any standard bus, such as a CAN bus, that is capable of communicating with the plurality of peripherals, or can include individual signal paths to individual peripherals. Peripherals can utilize their own power sources or the common power system 303.

Motion system 305 can include the control logic necessary for operating any of the motion systems described herein. For example, motion system 305 can include motor controllers in embodiments that use driven wheels. In other embodiments, motion system 305 can include the necessary logic to communicate with any active track systems necessary to provide a motive force to the carrier 300. In these embodiments, motion system 305 may be a software component executed by microcontroller 301 and utilizing communication system 315 to communicate with the track. Devices such as motors, actuators, electromagnets, and the like, that are controlled by motion system 305 can be powered by power system 303 in embodiments where these devices are onboard the carrier. External power sources can also provide power in some embodiments, such as embodiments where an LSM provides motive force by energizing coils in the track. In some embodiments, motion system 305 controls devices on or off the carrier to provide motive force. In some embodiments, the motion system 305 works with other controllers, such as controllers in the track, to coordinate motive forces, such as by requesting nearby coils in the track be energized or requesting the movement of local rollers. In these embodiments, motion system 305 can work together with communication system 315 to move the carrier.

Carrier 300 can include one or more sensors. In some embodiments, carrier 300 includes a collision detection system 312. Collision detection system 312 can include sensors at the front or back of a carrier for determining if it is getting close to another carrier. Exemplary collision detection sensors can include IR range-finding, magnetic sensors, microwave sensors, or optical detectors. Whereas many prior art pucks are round, carrier 300 may be directional, having a front portion and a rear portion. By having a directional geometry, carrier 300 can include a front collision detector and a rear collision detector.

In some embodiments, collision detection information can include information received via the communication system 315. For example, in some embodiments, the central controller for the track can observe the location and speed of carriers on the track and evaluate collision conditions and send updated directions to a carrier to prevent a collision. In some embodiments, nearby carriers can communicate their positions in a peer-to-peer manner. This allows carriers to individually assess the risk of collision based on real-time position information received from other carriers. It will be understood that in embodiments where the carrier receives trajectory information about other carriers, or decisions are made with the help of a centralized controller that has access to trajectory information of nearby carriers, the carriers need not be directional, and can include sensors or receivers that do not depend on a given orientation of a carrier.

Carrier 300 can also include a position decoder 313. This sensor can extrapolate the carrier's position as described herein. For example, position decoder 313 can include a camera or other optical means to identify landmarks in the track, or observe optical encoding in the track. In some embodiments, position decoder 313 can also include inertial sensors, magnetic sensors, or other sensors sufficient to determine a carrier's current position, direction, velocity, acceleration, and/or jerk.

Carrier 300 can optionally include a barcode reader 314. If equipped with barcode reader 314, carrier 300 can observe the barcode of its payload at the time the samples are loaded onto the carrier or at any time thereafter. This prevents the need for a carrier to stop at individual decision points to have the system read the barcode of a sample tube. By reading and storing the identity of the sample tube, or conveying this information to the overall system, a carrier may more efficiently traverse the track system because routing decisions can be made in advance of reaching a decision point. Alternatively, where a system knows the identity of the sample when it is placed onto the carrier, the system can include an external barcode reader and can convey the identity of the payload to the carrier for storage and memory 304 via communication system 315.

Communication system 315 can comprise any mechanisms sufficient to allow the carrier to communicate with the overall automation system. For example, this can include an XBee communication system for wireless communication using an off-the-shelf communication protocol, such as 802.15.4, any appropriate version of 802.11, or any standard or proprietary wireless protocol. Communication system 315 can include a transceiver and antenna and logic for operating an RF communication protocol. In some embodiments, communication system 315 can also include near field communication, optical communication or electrical contact components. Information conveyed via the communications system to/from carrier 300 is described throughout this application.

In some embodiments, the carrier can also include a status display module 316. The status display module 316 can include a controller and rewritable electronic display, such as an LCD panel or E-ink display. In some embodiments, the controller is treated as an addressable portion of memory, such that the microcontroller 301 can easily update the status display 316.

In some embodiments, the carrier also includes sample sensor 317. This sensor can be used to indicate the presence or absence of a fluid container in the carrier's tube bracket (which may also be referred to as a tube holder). In some embodiments, this is a momentary mechanical switch that is depressed by the presence of a tube and not depressed when a tube is absent. This information can be used to determine the status of a tube, which can assist in the display of status information by status display module 316.

Routing Exemplary Carriers in an Exemplary Analyzer

The desire for rapid transit times within an analyzer system can make routing difficult. In prior art systems, rapid routing is less critical because samples are generally stopped, singulated, and scanned at each decision point. In those systems, the routing decision for a given decision point can be made while the sample is stopped. Rapid routing decisions are generally desired, and may require determining a switching decision before a sample carrier reaches a decision point. Furthermore, because the carriers move at a rapid rate compared to the prior art, the control of the instantaneous trajectory of a sample carrier can be assisted by real-time processing in order to prevent spilling or damaging IVD samples. In some embodiments, substantially instantaneous trajectory observation and control is conducted on-board each carrier to facilitate real-time control, while the overall routing decisions are made by a central controller that manages a group of carriers. Therefore, in some embodiments, the carriers act like semi-autonomous robots that receive global routing instructions from a central controller, but make local motion decisions substantially autonomously.

For example, when a carrier receives a sample (e.g., a patient fluid sample or other payload) a central controller managing one or more carriers determines the schedule for that carrier and instructs the carrier where to go on the track of, for example, an in vitro diagnostics automation system. This instruction can be a next-hop instruction (e.g., identifying the next leg of a route), such as going to a given decision point, moving forward to the next decision point, or turning at a given decision point. In some embodiments, the instructions can include a complete or partial list of track segments and decision points to be traversed and whether to turn at each decision point. These instructions can be communicated to the carrier from a central controller via any conventional means, including wireless or contact electrical signaling, as explained throughout this disclosure.

While following the instructions, each carrier can make a determination of the appropriate velocity, acceleration, and jerk (as used herein, acceleration includes deceleration). This can include a real-time decision of whether the carrier must slow down to avoid collision or to enter a curve without causing excessive lateral forces, or slow down before the next decision point. These decisions can be made with the assistance of any on-board sensors, as well as external information received by the carrier, such as information about the position and trajectory of nearby carriers. For example, accelerometers and/or track encoding information can be used to determine the current velocity, acceleration, and jerk, as well as the current position of a carrier. This information can be used by each carrier to determine its trajectory and/or can be conveyed to other carriers. Collision detectors, such as RF rangefinders, can determine whether or not a potential collision condition exists to assist the carrier in determining whether it needs to slow down and/or stop. This collision determination can include trajectory information about the current carrier, as well as the trajectory information about surrounding carriers received by the current carrier through observation or by receiving information from a central scheduler for the track.

Figure 8:
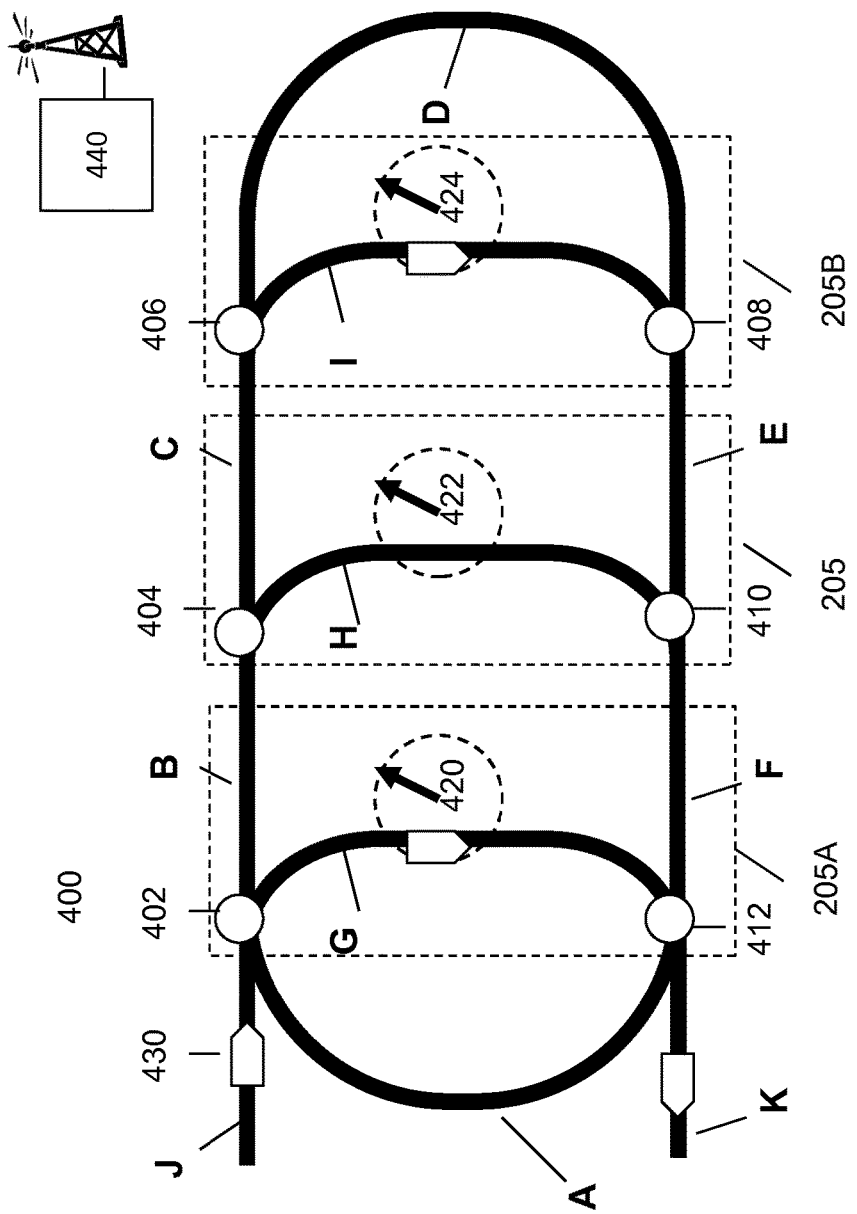
FIG. 8 is a diagrammatic view of exemplary routes in an exemplary track configuration that can be used for navigation of sample carriers in certain embodiments.

FIG. 8 shows an exemplary routing scenario in automation system 400. Carrier 430 receives routing instructions from central management processor 440 via RF signaling. Central management processor 440 can participate in monitoring and directing carriers, including issuing routing instructions and scheduling the movement and dispatch of carriers. Central management processor 440 can be part of the central controller and/or local controllers that interact with individual modules or situations. Central or local controllers can also act at the direction of central management processor 440. Central management processor 440 can include one or more processors operating together, independently, and/or in communication with one another. Central management processor 440 can be microprocessor, software operating on one or more processors, or other conventional computer means suitable for calculating the schedule for multiple carriers within the track system 400.

Central management processor 440 can receive position information from multiple carriers, as well as any sensor information from sensors in the track system 400 and/or information reported by the carriers. Central management processor 440 uses the status information of the carriers and track as well as the identity of samples or other payload carried by the carriers and the required assays to be performed by the system on these samples.

The exemplary track 400 shown in FIG. 8 includes a first curve segment A, that connects to straight segment B and a pullout segment G (e.g., a segment that serves a testing station), which serves analyzer/testing station 205A and pipette 420, via decision point 402. Segment B connects to straight segment C and a pullout segment H, which serves analyzer/testing station 205 and pipette 422, via decision point 404. Segment C connects to curved segment D, which serves sample handling station 205C, and pullout segment I, which serves analyzer/testing station 205B and pipette 424, via decision point 406. Segment D connects to straight segment E and the other end of pullout segment I, via decision point 408. That is, there are different paths between decision points 406 and 408—segments D and I, (where segment I is a pullout that can be used to deliver samples to interact with pipette 424). Segment E connects to straight segment F and the other end of pullout segment H, via decision point 410. Segment F connects to curved segment A and the other end of pullout segment G, via decision point 412. In some embodiments, track 400 includes input and output lanes J and K, which can be used to add or remove carriers at decision points 402 and 412.

In some embodiments, decision points 402-412 are passive forks in the track that carrier 430 can navigate to select a proper destination segment. In other embodiments, decision points 402-412 are active forks that can be controlled by carrier 430 or central management processor 440. In some embodiments, decision points 402-412 are electromagnetically controlled switches that respond to requests by carrier 430, such as via RF or near field communication. In some embodiments these electromagnetically controlled switches have a default position, such as straight, that the switch will return to once a carrier has been routed. By using default positions for decision points, a carrier may not need to request a position at each decision point, unless it needs to be switched at that decision point.

Scheduler/central management processor 440 assigns carrier 430 a first route, Route 1, to place the carrier 430 and its payload within reach of pipette 420. Carrier 430 is instructed to travel along segment J to decision point 402 and travel onto segment G to stop at a position accessible to pipette 420. In some embodiments, carrier 430 receives the instructions and determines its current location and trajectory to determine a direction and trajectory to use to reach decision point 402. Carrier 430 can also take into account that it will be making a hard right turn at decision point 402 onto segment G. In some embodiments, decision point 402 includes a switching mechanism in the track that can operate under the control of carrier 430. In these embodiments, carrier 430 communicates with the track on approach to decision point 402 to request switching onto segment G. In other embodiments, carrier 430 may have a steering mechanism (such as moveable guide wheel, directional magnets, asymmetric brakes, or the like) that allows carrier 430 to make a right turn onto segment G at decision point 402, without the assistance of an external gate integrated into the track. In these embodiments, carrier 430 engages the steering mechanism at decision point 402 to make the turn onto segment G.

Carrier 430 can determine its rough location—its current track section, such as section J, by reading encoding in the track, such as optical encoding, or RFID tags. In some embodiments, carrier 430 uses multiple means to determine its location within the track system 400. For example, RFID tags can be used to determine generally on which track segment the carrier 430 is located, while optical encoding or other precise encoding can be used to determine the position within that track segment. This encoding can also be used to determine velocity, acceleration, or jerk by observing changes in the encoding (e.g., derivatives from the position information).

Carrier 430 can use the identification of the current track section to determine the appropriate route to the destination section either by explicit instruction received by the central management processor 440 or by looking up an appropriate route in an onboard database in memory 304, as shown in the onboard control systems in FIG. 7. In some embodiments, the carrier 430 has an understanding of how to reach section G from section J based on a map stored in the memory of carrier 430 in memory 304. This map can include a simple lookup table or a tree of track sections where each node is linked by the corresponding decision points, or vice versa. For example, upon identifying that the carrier is currently in the track section J, the onboard database can inform carrier 430 to proceed to decision point 402 to be switched to the right onto section G.

As shown in FIG. 8, carrier 430 responds to instructions for Route 1 by proceeding onto section G and stopping at a position near pipette 420. Once the carrier 430 is stopped, it can receive additional instructions from the analyzer/testing station controlling pipette 420. For example, analyzer 205A can control pipette 420 and can instruct carriers on section G to position themselves at precise points along section G. This allows analyzer/testing stations to treat track sections as random-access queues. For example, once carrier 430 stops on section G, additional instructions can be conveyed via central management processor 440 or directly from analyzer 205A to the carrier 430 via RF transmission or other means, such as local optical or inductive/near field signals. These instructions can include halting while another carrier interacts with pipette 420, and subsequently proceeding to a position accessible to pipette 420, when analyzer 205A is ready to perform one or more assays on the sample carried by carrier 430.

Once analyzer/testing station 205A has finished interacting with the sample carried by carrier 430, additional routing instructions can be sent to the carrier 430 from the central management processor 440. For example, Route 2 can include routing instructions to proceed to section H to interact with pipette 422. In some embodiments, the routing tables contained within onboard memory 304 of carrier 430 have sufficient information about the track layout to allow the carrier to route itself to section H. In other embodiments, a list of routing steps can be transmitted to carrier 430 via central management processor 440. It will be appreciated that other embodiments can include conveying any subset of the route to carrier 430 and/or sending routing instructions in a piecemeal fashion, such that carrier 430 always knows the next routing step, and optionally subsequent routing steps.

In this example, carrier 430 receives a route list representing Route 2 from central management processor 440 instructing it to proceed via section G to decision point 412. At decision point 412, carrier 430 will initiate switching onto section A by interacting with a gate or by turning as described above. Carrier 430 can take into account curved track conditions on section G and section A to ensure that acceleration and jerk conditions do not exceed a threshold requirement for the sample it carries. This can prevent spillage or instability during transit. The route information received by carrier 430 then instructs carrier 430 to proceed through decision point 402 without turning. The trajectory used in Route 2 when approaching decision point 402 can be different (e.g., faster) from that used during Route 1, because carrier 430 knows that it does not need to make a sharp right turn onto section G. In some embodiments, this allows carrier 430 to approach decision point 402 with a substantially greater velocity during Route 2 than during Route 1. By traversing decision point 402 faster if carrier 430 is not turning, carrier 430 can complete Route 2 in less time than embodiments in which carrier 430 must slow down for possible switching at each decision point. This is an improvement over the prior art, where carriers are typically halted and singulated, regardless of whether the carrier is turning or not.

After passing decision point 402, carrier 430 proceeds onto section B. At decision point 404, carrier 430 proceeds to section C. At decision point 406, carrier 430 prepares and turns onto section I, where it stops for interaction with pipette 424. Like section G, section I can act as a queue for pipette 424 and carrier 430 can be controlled under local instruction by the analyzer/testing station 205B served by section I.

When pipette 424 is done interacting with carrier 430, central management processor 440 can provide new routing instructions to carrier 430 instructing carrier 430 to proceed onto an output path K. Route 3 can be handled in the same manner as Route 1 and Route 2. Upon receiving instructions for Route 3, carrier 430 proceeds down section I to decision point 408 where it turns back onto a main track section E and proceeds past decision point 410, track section F, and decision point 412 (without needing to slow down in some embodiments), and onto section K where the carrier 430 and/or the sample can be removed from the system by an operator. Carrier 430 can then be reused for samples at input section J. Upon receiving instructions for Route 4, carrier 430 proceeds down section D to sample handling station 205C and to decision point 408 where it turns back onto a main track section E and then proceeds the same as Route 3.

In some embodiments, each track section of FIG. 8 can be configured to include one or more speed zones. This may be represented as a speed or acceleration limit in software that maintains motion profiles for each carrier. For example, section D may be represented for trajectory control as a slow speed zone for all carriers to account for the inherent centripetal forces exerted by the track as carriers traverse section D. Similarly, track sections can include multiple speed zones within the track section, which may include motion profile rules. For example, a carrier may slow down responsive to software enforcement of rules that identify the latter portion of section C as a braking zone due to the upcoming speed limited zone in track section D. In some embodiments, software responsible for maintaining motion profile rules for carriers may take into account an upcoming speed zone and brake in an unlimited track section in anticipation. Furthermore, different track section portions can be represented as dynamic speed zones. For example, a stopping point for interaction with a pipette can be represented by a speed zone with a speed of zero for carriers that should stop at that location. This may allow trajectory enforcing software to automatically slow down the affected carrier as it approaches the stopping position.

Figure 9:
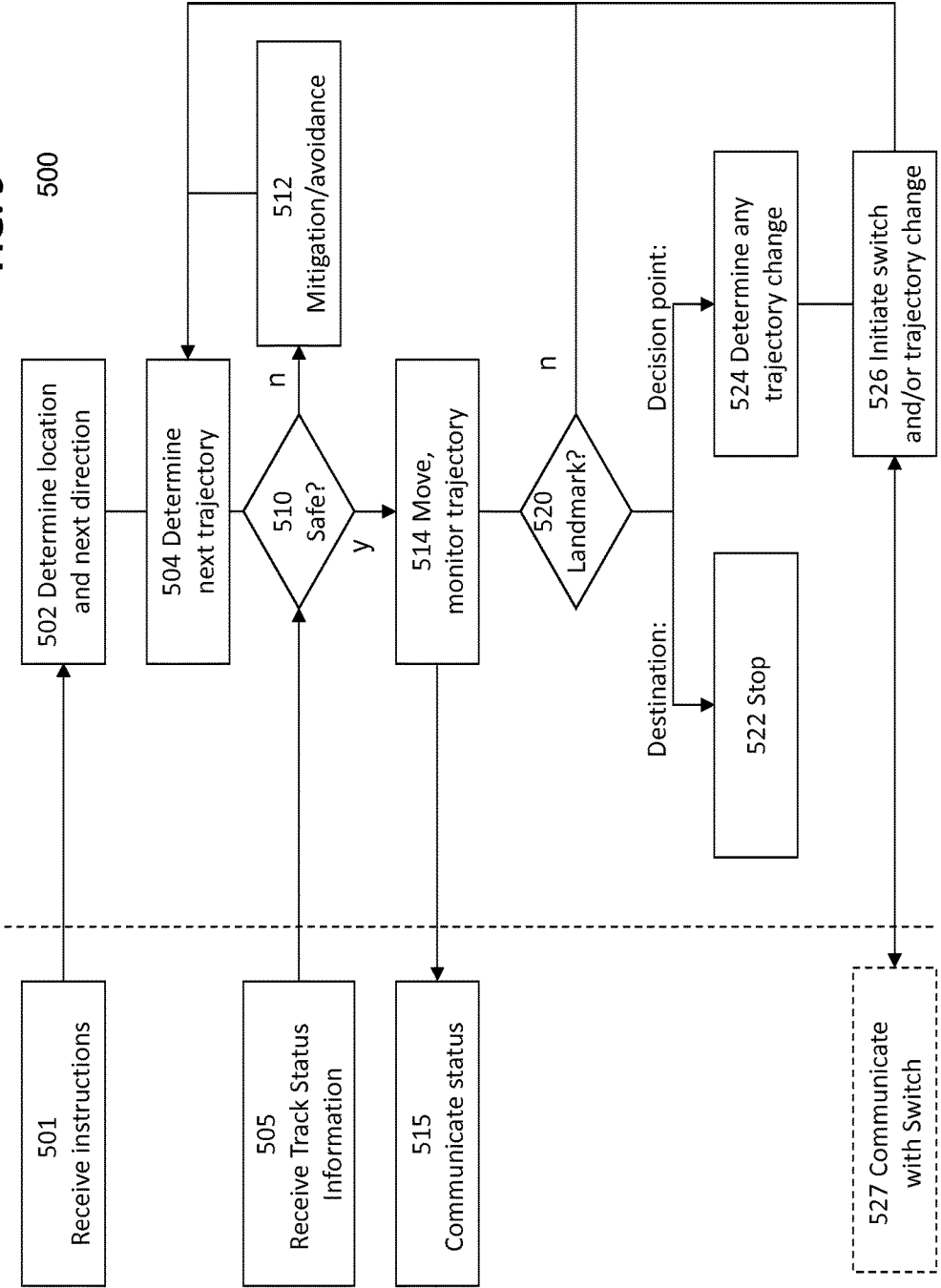
FIG. 9 is a flow diagram showing the operation of the navigation of sample carriers in certain embodiments.

FIG. 9 shows a general operational diagram of carrier 430 as it follows routing instructions. As can be seen in method 500, the actions can be taken by the carrier with minimal control by, or interaction with, a central scheduler, such as a central management controller. At step 501 the carrier receives routing instructions from, for example, a central scheduler. In this example, the routing instructions include enough information for the carrier to determine its entire route to a destination point in the track system. These instructions can include a list of all routing points, including decision points to turn at and sections to traverse. In some embodiments, routing instructions can include the destination point and onboard routing information can be used by the carrier to determine the best route to take. It will be appreciated that, when at least a main track is unidirectional, the routing calculation by the carrier is fairly simple and can comprise any known method including searching a tree of nodes and sections or searching a lookup table of possible route permutations.

These instructions can also include velocity and acceleration motion profiles for each section. In some embodiments, velocity and acceleration for each section of track can be calculated by the carrier based on its payload and based on information in an onboard database, such as length of track, curvature of track, location of decision points, the type of sample or payload being carried, and consideration of whether the carrier will turn or proceed in the same direction upon reaching a decision point. In some embodiments, the routing information received at step 501 also includes timing information to instruct the carrier when to begin transit and/or when to complete transit.

Upon receiving routing instructions and beginning transit, the carrier determines its current location and optionally the direction needed to begin its route at step 502. In a general sense, a carrier can only move in two directions, forward or backwards and, in some embodiments, initiate a turn while moving. Because of the simplified movement model, a carrier can begin its transit even if it only has a rough understanding of its current location, such as by acquiring the current track section by RFID information. In some embodiments, the carrier uses more precise encoding in the track to determine its current location within a track section before proceeding.

Once the current position and necessary direction is determined, the carrier can begin transit at step 504. By using an understanding of the location on the track, geometry of the current track, distance to the next decision point, type of sample/payload, and current velocity, the carrier can determine a safe acceleration profile to begin transit. For example, if a carrier is a large distance away from the next decision point and is currently stopped, the carrier can begin accelerating at a maximum acceleration for the sample. In some embodiments, the acceleration of the carrier is ramped up to avoid exposing the sample to a high degree jerk.

FIG. 10 shows an exemplary acceleration motion profile that can be used to limit jerk and acceleration, while minimizing transit time. By using a trapezoidal acceleration profile, acceleration is ramped up to avoid unnecessary jerk until acceleration reaches a safe amount that is less than a threshold amount to avoid damaging or spilling the sample. By ensuring that acceleration is less than a threshold amount, a carrier may have some acceleration available to mitigate collisions or handle other unexpected situations without exceeding an acceleration threshold for the payload. Generally, maximum velocity will be reached midway between a start point and a stop point. In some embodiments, there is no top speed for a straight section of track, but curved sections of track are governed by a top speed to prevent excessive lateral acceleration. These speed limits and acceleration thresholds may be known to an intelligent carrier, and may be accessible in onboard memory. The exact motion profile used by a carrier can vary depending on the payload being carried. For example, empty carriers or carriers transporting reagents or non-sample payloads may utilize a motion profile that has higher limits than a motion profile that carries a sample.

Unlike traditional friction tracks, which are governed by a fixed velocity of the track, some embodiments of present invention can enable dynamic acceleration profiles and allow carriers to move at much greater average velocity than the prior art. In some embodiments, it is generally desirable to limit the maximum transit time between any points within the track system to less than a portion of an operation cycle of the clinical analyzer. For example, if the maximum distance between any points on a track system is 25 m and the operation cycle time is 20 seconds, it may be desirable to ensure that the average velocity of the carrier, including all turns, acceleration, deceleration, starting, and stopping, is sufficient to traverse 30 m in 5 seconds or less, or 6 m/s (~2.1 km/hr). Because a majority of the time in transit is spent accelerating or decelerating, it will be appreciated that the maximum velocity of the carrier on a straightaway can be substantially higher than this average velocity.

Because jerk and acceleration should be limited for samples, real-time control of acceleration is desired. This goal is furthered by giving control of acceleration to the carrier itself so that it can monitor its current trajectory using accelerometers or other sensors. The carrier can dynamically change its trajectory based on track conditions such as location, traffic, and the need to slow down for an upcoming turn. In this manner, the carrier can be responsible for monitoring and controlling its own dynamic stability conditions.

Referring back to FIG. 9, at step 510, the carrier determines whether or not it is safe to continue accelerating or decelerating in accordance with the trajectory determined in step 504. Step 510 can include collision detection or checking for other unexpected obstructions or a system-wide or carrier-specific halt command. In some embodiments, the decision at step 510 is based on collision detection sensors, including RF rangefinders, but can also include status information about the track received from the central management controller or from other carriers at step 505. This status information can include, for example, position and trajectory information about surrounding carriers or updated commands such as a halt instruction or new route instructions.

If the carrier determines at step 510 that it is not safe to continue with the planned trajectory, the carrier can take steps to mitigate or avoid a collision at step 512. For example, if it is determined that the acceleration profile will place the carrier dangerously close to another carrier, the carrier can begin slowing down. In some embodiments, the decision to slow down to avoid collision is based on an extrapolation of the current trajectory and the observed trajectory of the other carrier. If it is determined that the current trajectory will cause the carrier to come within an unsafe following distance from the carrier ahead of it, the mitigation procedure will be initiated. In some embodiments, each carrier is modeled as having a collision zone into which it is unsafe to enter. This collision zone moves with the carrier. If a carrier senses that it will invade a collision zone of another carrier (or another carrier will invade the instant carrier's collision zone), the carrier can mitigate the collision by decelerating (or accelerating to avoid a rear end collision in some embodiments).

After the carrier decelerates/accelerates to mitigate a collision, the carrier proceeds back to step 504 to determine an updated trajectory that takes into account the new collision avoidance conditions. If no unsafe condition is detected, the carrier proceeds with implementing its trajectory at step 514 (e.g., proceed with a portion of the trajectory before repeating steps 504-510 to allow for continuous monitoring of conditions). This can include accelerating or decelerating and observing track encoding and accelerometer information to determine its current status and trajectory. In some embodiments, the carrier will communicate its current status, including location, trajectory, and/or planned trajectory to the central controller and/or other carriers to assist in routing and collision avoidance at step 515.

As the carrier begins iteratively implementing its planned trajectory, it observes the track for upcoming landmarks, such as its terminal destination or an upcoming decision point at step 520. These landmarks can be identified via important features in the track, such as a warning or braking LED, by extrapolating the distance to a landmark from the observed encoding, or by some combination thereof. If no landmark is upcoming, the carrier continues to step 504 and continues iteratively calculating and implementing a planned trajectory.

In this example, there are two types of important landmarks. The first landmark is the destination of the carrier. The carrier can determine if it is nearing its destination based on track encoding or a landmark feature such as an LED and uses information to begin stopping or complete a stopping procedure at step 522. For example, a carrier may be instructed to stop at a precise location accessible to a pipette. This precise location may include an LED in the wall or floor of the track to assist a carrier in the stopping at a precise location with millimeter accuracy. In some embodiments, the calculated trajectory at step 504 is used to get a carrier in a rough location of its destination, while a stopping procedure at step 522 is used to determine the precise stopped location, such as by searching for a nearby LED landmark and stopping at the appropriate position.

Another important landmark is a decision point. Encoding or warning LEDs in the track can convey the position of an upcoming decision point to a carrier. For example, a central management controller may illuminate an LED at a braking position on the track some distance before a decision point to alert the carrier to decelerate to prevent unnecessary acceleration or collision at decision point. In other embodiments, the carrier extrapolates the relative position of an upcoming decision point from the track encoding and uses this distance to update its trajectory, if necessary, at step 524. At step 524, a carrier determines the relative location of a decision point and determines, based on its routing information, if the carrier will be turning or proceeding at the decision point. If the carrier will be turning, it may be necessary to update the trajectory to begin decelerating so that the velocity of the carrier is slow enough when it turns at the decision point to prevent unnecessary lateral forces that could harm or spill a sample.

In many instances, the carrier will be proceeding past the decision point without turning. In these instances, it may not be necessary to update the trajectory and the carrier can continue at its current velocity or even continue to accelerate through the decision point.

If the carrier determines that it needs to turn at the upcoming decision point, the carrier can slow down and initiate the turn at step 526. In some embodiments, the carrier is only capable of forward or backwards movement without assistance. In these embodiments, the carrier or central management controller can communicate with a switching mechanism at the decision point, at step 527, to ensure that any mechanical or electromagnetic devices in the track system 400 are engaged to direct the carrier in the appropriate direction when it traverses the decision point.

Examples of devices in the track can include mechanical switches that block one path at a fork and assist the carrier in turning down the other path at the fork (like a railroad switch that can be mounted to rails or a gate when the track is shaped like a trough), magnets that pull the carrier in one direction or another, or changing signaling in the path that assists the carrier in turning, such as an LED that the carrier follows or an LCD or e-ink panel in the track that includes a line that can be followed by the carrier if the carrier is equipped with traditional line-following capabilities. Unlike prior art configurations that singulate, scan, and push individual carriers after they stop at a decision point, some embodiments of the present invention can negotiate a turn before a carrier physically arrives at a decision point. This can allow a carrier to proceed at a velocity limited by the curvature of a turn, rather than having to stop or wait for other mechanisms in order to turn.

In embodiments where a carrier has some steering capability and can turn at a decision point without the assistance of the next internal switch, the carrier can engage its steering mechanism to direct it to the appropriate path upon approaching the decision point. After turning at the decision point (or proceeding without turning) a carrier returns to step 504 to determine its next trajectory.

Handling Priority Samples.

By utilizing the automation systems and methods described throughout, normal and higher priority samples can be transported within an analyzer. Higher priority samples may be processed ahead of lower priority samples without disrupting queues of normal priority samples. This can be accomplished in a number of ways, including eliminating physical queues within the system, allowing samples to freely flow without having large numbers of samples accumulating any given position in the system. This may allow high priority samples to move through the system without physically affecting normal priority samples, allowing higher priority samples to simply be scheduled ahead of lower priority samples in software.

However, in some embodiments, queues may still exist on local track portions, such as sidecars and internal paths that intersect main track portions. With respect to FIG. 8, main track portions may include track sections A through F, while internal sidecars G, H, and I may act as local track portions. In some embodiments, software and hardware configurations attempt to avoid physical queues from forming on main track portions A through F, while physical queues may be acceptable during operation on track portions G through I. These local queues may serve pipettes 420 through 424.

To avoid delays caused by queues, system 400 in FIG. 8 can be modified to allow higher priority samples to access pipettes 420 through 424 while on main track portions A through F. This may allow higher priority samples to avoid local traffic, sticking to less congested main track portions. Higher priority samples can simply traverse the loop of the automation system, allowing the samples to quickly move into the automation system to be processed and move out, without causing lower priority samples to be flushed to main track portions, disturbing order and creating additional traffic.

Figure 11:
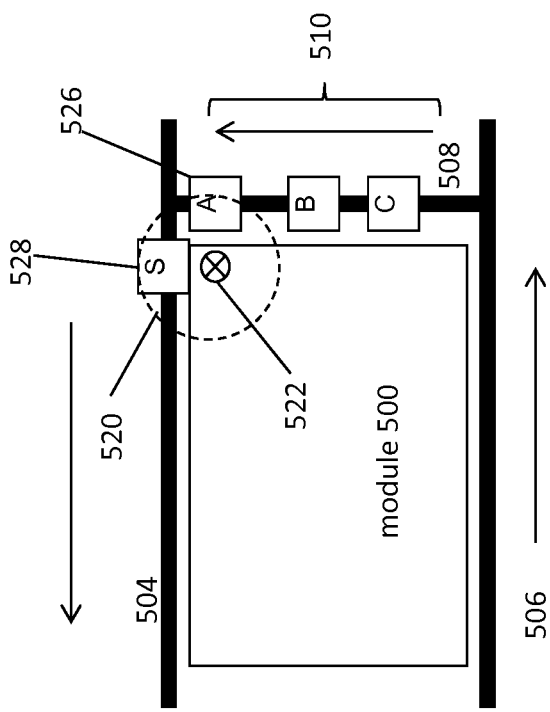
FIG. 11 is a diagrammatic view of an exemplary automation system for use with some embodiments.

FIG. 11 shows an example of one way that higher priority samples may be handled without waiting in a local queue. In this example, module 500 sits near main track portions 504 and 506. Local track portion 508 intersects these main track portions, allowing normal priority samples to be serviced in queue 510. Samples generally move in this exemplary automation system in the direction of the arrows. Queue 510 can be a physical FIFO queue, but it should be appreciated, that the software scheduling mechanisms disclosed herein can be used to create a random access queue by cycling samples into and out of local track portion 508, utilizing main track portions to reorder samples.

Module 500 is serviced by a pipette 520. This pipette is an exemplary instrument that interacts with fluid vessels on carriers on the automation system. These fluid vessels may include patient samples, reagents, calibration fluids, or any other suitable fluid. Pipette 520 can aspirate portions of the samples and dispense the aspirated portions within module 500 to perform various processing tasks. These portions may be placed into reaction vessels, for instance.

In this embodiment, pipette 520 is a rotary pipette. A rotary pipette includes a pipette assembly that includes an actuated probe that may be moved up and down to allow the probe tip to be inserted into fluid vessels and withdrawn therefrom. In some embodiments, the pipette assembly may also be able to actuated horizontally to change the radius of rotation. In some embodiments, the radius of rotation is fixed. A rotary pipette generally includes a rotation mechanism that allows an arm that holds the pipette assembly to be rotated about a center point. This example, the pipette assembly may be rotated about point 522, which provides a center point for rotary pipette 520.

Whereas the rotary pipettes 420, 422, and 424 in FIG. 8 are illustrated as able to rotate above a local track section, but not a main track section, pipette 520 has been placed with a center point position 522 that allows the pipette assembly to be rotated in proximity to one or more positions on main track 504 and local track 508. This may be advantageous for accessing high priority samples, such as STAT samples, and normal priority samples, without disturbing sample queues.

An example of this advantage can be seen with respect to STAT sample S and normal priority sample A. Sample A resides in queue 510. Behind it, samples B and C are awaiting processing by interaction with pipette 520. When sample A reaches location 526 on track 508, pipette 520 may rotate above this location and aspirates a portion of sample A. Once sample A has been processed, samples B and C can be positioned at location 526 for similar processing. Meanwhile, STAT sample S is a higher priority sample and may need access to module 500. STAT sample S may stop at location 528 on main track portion 504. Pipette 520 may be rotated about center point 522 to be positioned above location 528. Pipette 520 may then aspirate portion of STAT sample S. Once the aspirated portion has been taken, STAT sample S may then move along main track 504 to its next destination. Meanwhile, samples A, B and C can sit idle on track portion 508. The samples do not need to be flushed onto the main track and their order may be preserved. The only impact of STAT sample S on the queue 510 is that queue 510 may need to wait an additional operation cycle because STAT sample S was processed before the samples. Accordingly, by providing access locations 526 and 528 for differing priority samples to access pipette 520, priority samples can be processed without affecting local queues of lower priority samples.

Figure 12:
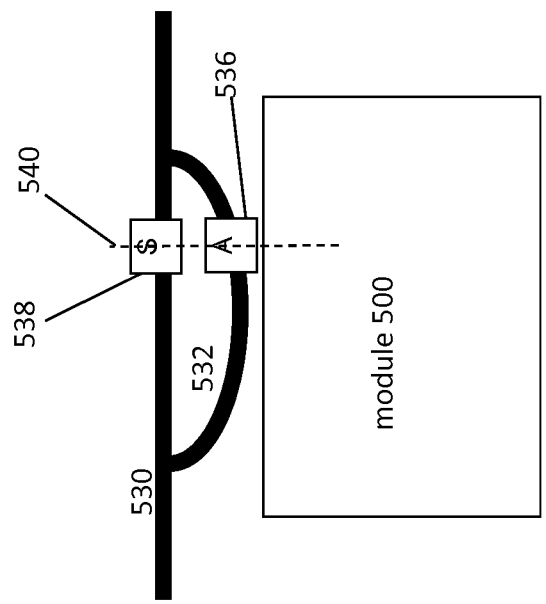
FIG. 12 is a diagrammatic view of an exemplary automation system for use with some embodiments.

FIG. 12 shows an alternate embodiment that utilizes same principle of providing to differing access locations for differing priority samples. In this example, module 500 is served by a sidecar 532 that allows samples to pull off of main track portion 530. Normal priority samples, such as sample A, can wait on sidecar 532 for processing. A queue similar to queue 510 may form on sidecar 532. In this example, a linear pipette 540 may be used. A linear pipette is a pipette that includes a pipette mechanism that may be actuated linearly in the horizontal direction. This may allow a pipette to be extended and retracted to allow sample portions to be aspirated and moved into analyzer systems within module 500. In this example, pipette 540 can be moved above location 536 to interact with normal priority samples or to location 538 on main track portion 530 interact with high priority samples. This allows high priority samples to remain on main track portions, without having to disturb local queues on local sidecars, such as sidecar 532.

It should be appreciated that the principles shown in FIGS. 9 and 10 can be applied to many different track geometries. Furthermore, provided a pipette can be configured to access multiple locations, using conventional actuation means, such as rotary pipettes and linear pipettes, no additional or specialized hardware may be needed in the automation system. Provided that a high priority sample has a means for stopping on a main track portion at the access location for the pipette (or other instrument) these principles can be used simply by locating and configuring a pipette to be able to access multiple locations. Exemplary means that may be used to stop a high priority sample at an access location include using the independent carrier mechanisms discussed throughout. Furthermore, physical stops may also be used in some embodiments. For example, if friction tracks are used, a hard stop that temporarily singulates a STAT sample at the access location may be used. In some embodiments, this hard stop may be configured to only be engaged when a STAT sample is nearby or present. This may allow the hard stop to be used without disrupting the normal flow of samples on the main track or creating a local buffer as samples accumulate during normal operation.

Figure 13:
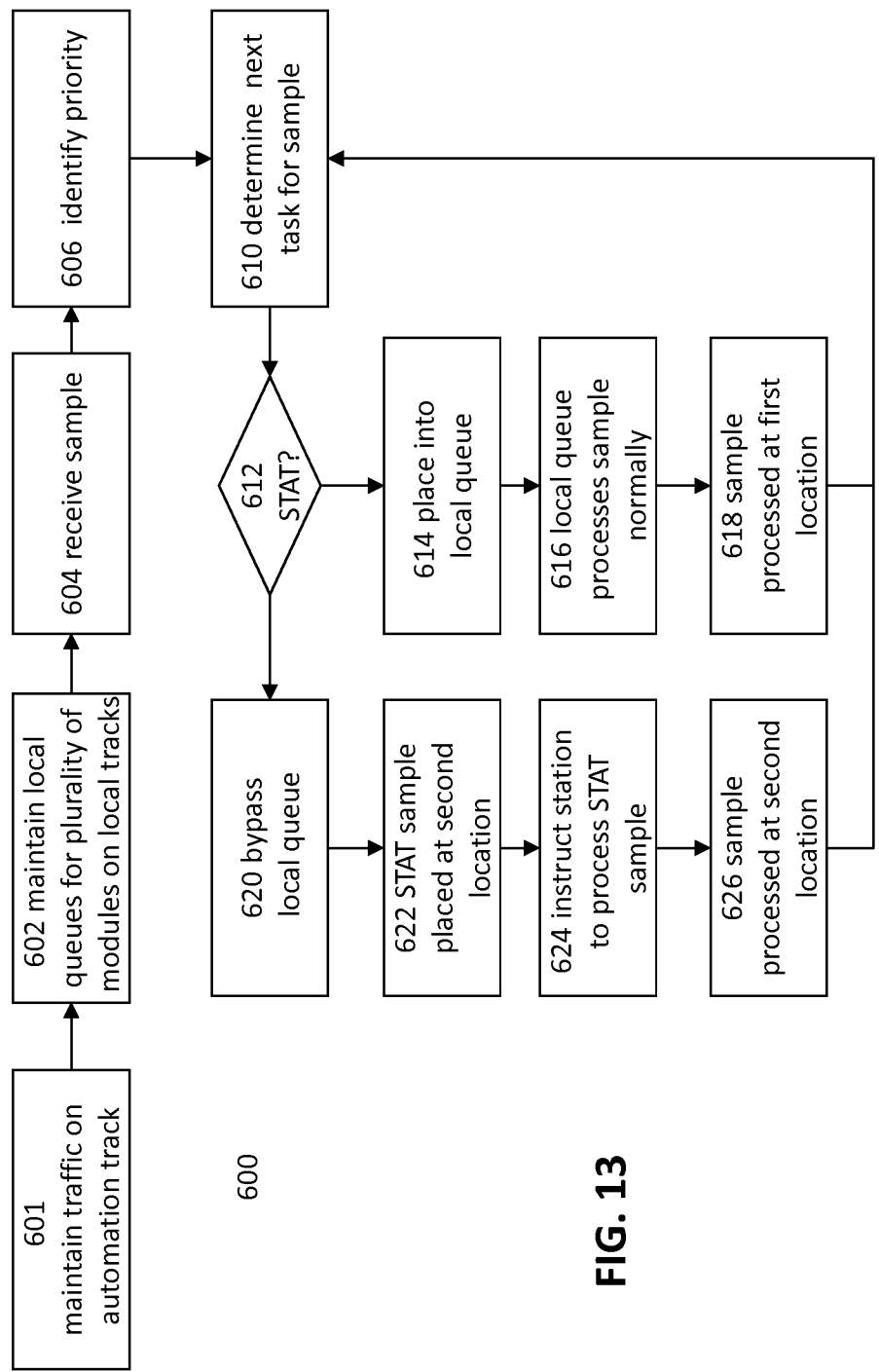
FIG. 13 is a flow diagram showing the handling of different priority samples in certain embodiments.

FIG. 13 shows an exemplary method 600 for utilizing multiple access locations to allow higher priority samples to be handled without disturbing local queues. At step 601, a processor, such as central processor 440 maintains traffic on the automation system. This traffic can include sample vessels or other fluid vessels transported by carriers. These steps may be performed using any of the methods disclosed herein. At step 602, one or more processors can maintain local queues for each of a plurality of modules or stations within an analyzer. These queues may be generally limited to local track sections, such as sidecars to limit the amount of accumulate samples on main track portions.

At step 604, a processor receives the identity of the sample. This may occur via any of the methods for reporting the identity of the sample to processor disclosed herein, such as by reporting a scanned barcode when a sample is placed into a carrier and associating the identity of the sample with readable information, such as RFID tags, associated with the carrier. At step 606, the processor can then use this identity information to determine a priority for the sample. In some embodiments, the identity information includes information about the sample that includes priority. In some embodiments, the priority may be retrieved from a database based on the identity of the sample.

Using a priority and identity of the sample, a processor may then determine a schedule of tasks for that sample. These tasks may be the tasks necessary for completing a test panel required for that sample. Tasks may include going to multiple modules for processing. At step 610, the processor utilizes the schedule of tasks for each sample to identify a next task to be completed for that sample. The processor then undertakes steps to carry out that task. At step 612, the processor determines whether the task needs to be completed with higher priority for that sample.

If not, method 600 proceeds to step 614. At step 614, the processor directs the automation system to place the sample into a local queue. This will be the normal course of action for normal priority sample. Once in that local queue, at step 616, one or more processors that handle the queue can then process that sample using normal queue logic, such as by treating samples within a queue on a FIFO basis. At step 618, once a sample reaches the head of the queue or is the next sample to be processed, the local station processes the sample by placing the sample at a first access location to interact with a local instrument to complete the task. That instrument then completes the task.

If, on the other hand, the task is to be completed on a high priority basis, as determined by step 612, the sample will be positioned by the automation system so as to bypass a local queue for an instrument, at step 620. This can include moving a sample around a main track without moving that high-priority sample on to local sidecars for processing. At step 622 the high priority sample is positioned by the automation system at a second access location that is accessible to the instrument. This access location can be on a main track portion or at another location that allows the high priority sample to be positioned without being limited by samples of a local queue. Once positioned at the second access location, at step 624, a processor may instruct the instrument to move to the second location and process the high priority sample. At step 626, the sample is processed, such as by aspirating a portion of the sample using a pipette and moving that aspirated portion into an analyzer module. The sample may then be moved to the next station for processing. Once samples are processed at steps 618 or 626, method 600 returns to step 610 to determine the next step to finish all scheduled tasks for each sample.

It should be appreciated that, in some embodiments, there may be multiple levels of priority among samples. In some embodiments, several levels of priority may be used. In these embodiments, a corresponding number of access locations can be provided by the automation system. For example, a low priority sample may be placed in a normal queue on a side car, while a higher priority queue on another sidecar may be used for medium priority samples, and STAT samples made the accessed via the main track. In these embodiments, medium priority queues may be accessed before low priority queues, which may limit the size requirements needed to service these queues and may limit the occurrence of bottlenecks in these queues. It should also be appreciated that the geometries used for providing a plurality of access locations for multiple sample priorities need not be limited to the geometries disclosed herein. Access locations may be arranged in any suitable arrangement that may be dictated by the application of those embodiments.

Embodiments of the present invention may be integrated with existing analyzers and automation systems. It should be appreciated that carriers may be configured in many shapes and sizes, including layouts and physical configurations suitable for use with any contemplated analyzer or instrument. For example, in some embodiments, a carrier may include multiple slots for carrying multiple samples around an automation track. One embodiment, for example, may include a physical layout of a tube-holding portion of a carrier with multiple slots in one or more transport racks. Each rack may include multiple slots (e.g., five or more slots), each slot configured to hold a tube (e.g., a sample tube).

Although the invention has been described with reference to exemplary embodiments, it is not limited thereto. Those skilled in the art will appreciate that numerous changes and modifications may be made to the preferred embodiments of the invention and that such changes and modifications may be made without departing from the true spirit of the invention. It is therefore intended that the appended claims be construed to cover all such equivalent variations as fall within the true spirit and scope of the invention.

What is claimed is:

1. A method of processing patient samples on a track system comprising an external track which transport the samples and that forms an outer loop around the periphery of a plurality of analyzer modules wherein each analyzer module comprises analytical hardware configured to perform diagnostic assays on the samples, and a plurality of internal track portions, each internal track portion intersecting the external track to create a respective internal path along which samples are transported from one side of the outer loop to the other, the method comprising:
   handling, on a first internal track portion, a queue of samples for processing by a first module of the plurality of analyzer modules by moving samples bidirectionally on the first internal track portion;
   transporting a priority sample along the external track to a priority location on the outer loop of the external track, the priority location being accessible for processing the priority sample by the first module;
   processing, by a pipette of the first module, the pipette processing each sample by aspirating a portion of each sample, the queue of samples along the first internal track portion, and processing, by the pipette of the first module, the priority sample while it is at the priority location,
   wherein the pipette in the first module processes the priority sample having higher priority at the priority location while the queue of samples remains on the first internal track portion and resumes processing of the queue of samples along the first internal track portion upon completion of processing the priority sample.

2. The method of claim 1, wherein the pipette in the first module is positioned on a rotating device, wherein the rotating device is configured to rotate between positions allowing for processing on the first internal track portion and the priority location.

3. The method of claim 1, wherein the pipette in the first module comprises a linearly extending pipette configured to allow for processing on the first internal track portion and at the priority location.

4. The method of claim 1, wherein the first module comprises at least one of: (i) a sample handling module comprising hardware configured to place and pick sample vessels into and out of carriers on the track system; (ii) an immunoassay module comprising analytical hardware configured to perform immunoassays of the samples; and (iii) a clinical chemistry module comprising analytical hardware configured to perform clinical chemistry assays of the samples.

5. An automation system for use in transporting patient fluid samples between analyzer modules for processing thereof, the system comprising:
   a plurality of analyzer modules wherein each analyzer module comprises analytical hardware configured to perform diagnostic assays on the samples;
   a track system comprising:
      an external track forming an outer loop around the periphery of the analyzer modules along which samples are transported, and
      a plurality of bidirectional internal track portions, each internal track portion intersecting the external track to create a respective internal track along which samples are transported from one side of the outer loop to the other;

at least one processor; and each of the plurality of analyzer modules comprising at least one section of the external track, at least one internal track portion, a pipette that processes each sample by aspirating a portion of each sample and is configured to interact with samples at a priority position on the at least one section of the external track and on the at least one internal track portion, and module hardware configured to further process each sample once the pipette interacts with each sample, wherein when the plurality of modules are connected together, the sections of the external track comprise a continuous external track, wherein the pipette of a first module is configured to process a queue of samples along a first internal track portion and a priority sample at a first priority position of the external track, and the at least one processor is configured to control the pipette in the first module to process the priority sample having higher priority at the first priority position of the first module while the queue of samples remains on the first internal track portion and to resume processing of the queue of samples along the first internal track portion upon completion of processing the priority sample.

6. The system of claim 5, wherein the pipette in the first module is positioned on a rotating device, wherein the rotating device is configured to rotate between positions allowing for processing on the first internal track portion and the priority position of the first module.

7. The system of claim 5, wherein the pipette in the first module comprises a linearly extending pipette configured to allow for processing on the first internal track portion and at the priority position.

8. The system of claim 5, wherein the first module comprises: (i) a sample handling module wherein the module hardware is configured to place and pick sample vessels into and out of carriers on the track system; (ii) an immunoassay module wherein the module hardware is configured to perform immunoassays of the samples; or (iii) a clinical chemistry module wherein the module hardware is configured to perform clinical chemistry assays of the samples.

9. An automation system comprising:

a plurality of analyzer stations each comprising a pipette configured to obtain an aspirated portion of a patient sample and analytical hardware configured to perform an assay on the aspirated sample portion;

a plurality of automation track portions that are together configured to provide one or more paths between the plurality of analyzer stations, the track portions including outer track portions that form an outer loop around the outside of the plurality of analyzer stations and bidirectional internal track portions that pass across one of the plurality of analyzer stations from one side of the outer loop to the other;

a plurality of carriers, each configured to traverse the plurality of track portions to transport at least one of a plurality of fluid vessels containing patient sample fluids along the one or more paths to each of the plurality of stations; and one or more processors configured to, for each of the plurality of fluid vessels:

determine a priority of the fluid vessel, upon determination that the fluid vessel is of a first priority, direct a carrier of the plurality of carriers holding the fluid sample to stop at a first location on a first internal track portion, upon determination that the fluid vessel is of a second, higher priority, direct the carrier to stop at a second location on a second outer track portion, and request, from an analyzer station from the plurality of analyzer stations, aspiration and processing of a fluid contained in the fluid vessel at the corresponding first and second location, wherein both the first and second locations are accessible to the pipette of the one analyzer station from the plurality of analyzer stations.

10. The system of claim 9, wherein the pipette of the one analyzer station is positioned on a rotating device, wherein the rotating device is configured to rotate between positions allowing for processing of fluids at either of the first and second locations.

11. The system of claim 9, wherein the pipette of the one analyzer station is positioned on a linearly extending device, wherein the linearly extending device is configured to extend between positions allowing for processing of fluids at either of the first and second locations.

12. The system of claim 9, further comprising a sample handling station having hardware configured to place and pick sample vessels into and out of the plurality of carriers.

13. The system of claim 9, wherein the first location corresponds with the head of a queue of carriers on the first internal track portion.

14. The system of claim 13, wherein the second location is positioned such that higher priority fluid vessels may be positioned at the second location without first flushing the queue.

15. The system of claim 9, wherein the one or more processors are further configured to only direct carriers onto the first track portion if they carry a sample vessel of the first priority.

16. The system of claim 9, wherein the each analyzer station comprises: an immunoassay station, wherein the analytical hardware is configured to perform one or more immunoassays; or a clinical chemistry station, wherein the analytical hardware configured to perform one or more clinical chemistry assays.

* * * * *